(12) United States Patent
Liu et al.

(10) Patent No.: US 10,758,585 B2
(45) Date of Patent: Sep. 1, 2020

(54) BEAUTYBERRY TOTAL GLYCOSIDES EXTRACT AND PREPARATION METHOD AND USE THEREOF

(71) Applicant: Suzhou Neupharma Co., Ltd., Suzhou, Jiangsu (CN)

(72) Inventors: Jingge Liu, Jiangsu (CN); Yijun Cheng, Jiangsu (CN); Jinguo Cao, Jiangsu (CN); Yongliang Zhu, Jiangsu (CN); Xiangping Qian, Jiangsu (CN)

(73) Assignee: Suzhou Neupharma Co., Ltd., Suzhou (CN)

( * ) Notice: Subject to any disclaimer, the term of this patent is extended or adjusted under 35 U.S.C. 154(b) by 211 days.

(21) Appl. No.: 15/937,519

(22) Filed: Mar. 27, 2018

(65) Prior Publication Data

US 2018/0214500 A1 Aug. 2, 2018

Related U.S. Application Data

(62) Division of application No. 14/443,634, filed as application No. PCT/CN2013/086532 on Nov. 5, 2013, now abandoned.

(30) Foreign Application Priority Data

Nov. 19, 2012 (CN) .......................... 2012 1 0468493

(51) Int. Cl.
*A61K 36/53* (2006.01)
*A61K 31/7032* (2006.01)

(52) U.S. Cl.
CPC .......... *A61K 36/53* (2013.01); *A61K 31/7032* (2013.01); *A61K 2236/00* (2013.01)

(58) Field of Classification Search
None
See application file for complete search history.

(56) References Cited

U.S. PATENT DOCUMENTS

2015/0297659 A1   10/2015   Liu et al.

FOREIGN PATENT DOCUMENTS

| CN | 101036733 A | * | 9/2007 |
| CN | 101623394 A | | 1/2010 |
| CN | 101797307 A | | 8/2010 |
| CN | 102258637 A | | 11/2011 |
| CN | 102266277 A | | 12/2011 |
| CN | 102283947 A | | 12/2011 |
| WO | 2014/075570 A1 | | 5/2014 |

OTHER PUBLICATIONS

Wang Shu-Dong et al., Extraction and purification of total flavonoids from folium callicarpae pedunculatae with macroporous resin. J Med Postgra, vol. 24., No. 4, Apr. 2011 pp. 398-402.
Lu Chun-Hua et al., Water-soluble constituents from Callicarpa pedunculate. Chinese Journal of Natural Medicines, vol. 6, No. 3, May 2008, pp. 176-178.
Liu Jingjing et al., Rapid analysis of Callicarpa L. using direct spray ionization mass spectrometry. Journal of Pharmaceutical and Biomedical Analysis, vol. 124, May 30, 2016, pp. 93-103.
Extended European Search Report dated May 10, 2016 for European Patent Application Serial No. 13855773.1.
International Search Report for International Patent Application Serial No. PCT/CN2013/086532 dated Jan. 23, 2014 (search completed on Jan. 13, 2014).

* cited by examiner

*Primary Examiner* — Susan Hoffman
(74) *Attorney, Agent, or Firm* — K&L Gates LLP; Louis C. Cullman; Hal Gibson

(57) ABSTRACT

Disclosed is a composition comprising an beautyberry total glycosides extract, and a method of preparation thereof, and the use of the composition thereof in preparing drugs for treating neurodegenerative diseases or skin diseases. The extract thereof is prepared from the leaves of *Callicarpa cathayana* H.T. Chang or *Callicarpa formosana* Rolfe, and contains 18% to 45% verbascoside and 15% to 40% Arenarioside.

6 Claims, 14 Drawing Sheets

BEAUTYBERRY TOTAL GLYCOSIDES EXTRACT AND PREPARATION METHOD AND USE THEREOF

RELATED APPLICATION

This application is a divisional of U.S. patent application Ser. No. 14/443,634, filed on May 18, 2015, now abandoned, which is a 371 of PCT/CN2013/086532, filed Nov. 5, 2013, which claims priority to CN201210468493.2, filed Nov. 19, 2012.

TECHNICAL FIELD

The present invention relates to the field of traditional Chinese medicine, and particularly to a beautyberry total glycosides extract and a preparation method and use thereof.

BACKGROUND ART

Beautyberry is a generic term of plants of the genus *Callicarpa*, family Verbenaceae, which has a variety of species, about 35 of them in China, and has extensive distribution. Ingredients contained in beautyberry are mainly flavonoid, terpenoid, phenylethanoid glycosides and volatile oils, and the like. Phenethyl alcohol glycosides are chemical ingredients with high concentration in beautyberry. Phenylethanoid glycosides are also known as phenylpropanoid glycoside compounds because they are mainly hydrocinnamoyl aglucon. It has been reported that the phenylethanoid glycosides have pain-relief, antisepsis, and antiphlogosis, antitumor, antiviral, antioxidation, hepatoprotection, and base repair effects. Phenylethanoid glycosides have evident amelioration effects on diabetes, related diseases, low learning capacity, and the like. With intensive studies on the phenylethanoid glycoside ingredients in recent years, more reports indicate that phenylethanoid glycoside compounds have effects in prevention and treatment of neurodegenerative diseases, and particularly in amelioration of senile dementia, Parkinson's disease. Chinese patent application No. CN200710040195.2 reports preparation of a broomrape total glycosides (phenylethanoid glycoside ingredients) extract from broomrape, and reports use of the extract in the treatment of Parkinson's disease. Chinese patent CN201010146367.6 discloses preparation of an extract with forsythiaside B and verbascoside as main characteristic ingredients from aerial parts of *Callicarpa kochiana*, and discloses use of the extract in drugs for treating senile dementia.

However, broomrape is an endangered and rare traditional Chinese medicinal material with limited production. *Callicarpa kochiana* is based on wild types and has low production. Concentration of phenylethanoid glycoside ingredients in the two medicinal materials is low, so that preparation of phenylethanoid glycoside ingredients with broomrape and *Callicarpa kochiana* as raw materials suffers from high costs of production, and thus is not suitable for sustained development. Therefore, preparation of drugs for treating diseases such as neurodegenerative diseases from medicinal materials having abundant resources, low prices and high contents of phenylethanoid glycoside substances is desirable. In addition, because phenylethanoid glycoside substances have wide pharmacological activity, new efficacy and therapeutic effects of the phenylethanoid glycoside substances are also worthy of further development.

SUMMARY OF THE INVENTION

An objective of the present invention is to provide a beautyberry total glycosides extract derived from *Callicarpa cathayana* H.T. Chang or *Callicarpa formosana* Rolfe. The extract has phenylethanoid glycoside ingredients verbascoside and Arenarioside as characteristic active ingredients, and has therapeutic efficacy against neurodegenerative diseases. In addition, the extract also has therapeutic efficacy against eczema or dermatitis.

The present invention provides the following technical solutions.

1. A beautyberry total glycosides extract, containing 18% to 45% verbascoside and 15% to 40% Arenarioside based on weight, wherein the extract is prepared from leaves (preferably dried leaves) of *Callicarpa cathayana* H.T.Chang or *Callicarpa formosana* Rolfe.

2. The beautyberry total glycosides extract according to the technical solution 1, containing 28% to 45% verbascoside based on weight.

3. The beautyberry total glycosides extract according to the technical solution 1 or 2, containing 28% to 38% verbascoside based on weight.

4. The beautyberry total glycosides extract according to anyone of the technical solutions 1 to 3, containing 24% to 40% Arenarioside based on weight.

5. The beautyberry total glycosides extract according to anyone of the technical solutions 1 to 4, containing 25% to 35% Arenarioside based on weight.

6. A preparation method of the beautyberry total glycosides extract of anyone of the technical solutions 1 to 5, including the following steps:

(1) pulverizingleaves (preferably dried leaves) of *Callicarpa cathayana* H.T. Chang or *Callicarpa formosana* Rolfe, and extracting with a solvent 1 to 3 times, wherein the solvent is water, alcohol, or a mixture of water and alcohol;

(2) combining extract liquors from each extraction, concentrating under reduced pressure to remove the organic solvent in step (1); adding therein water in an amount of 0.5 to 2 times volume, letting the extract stand overnight, then centrifuging or filtering to obtain supernatant; and (3a) passing the supernatant through a chromatographic column packed with a resin filler, washing with water and/or a dilute alcohol aqueous solution to remove impurities, then eluting with a high-concentration alcohol aqueous solution, collecting eluent, concentrating under reduced pressure, and drying, so as to obtain the beautyberry total glycosides extract; or (3b) extracting the supernatant with an organic solvent, concentrating the organic phase under reduced pressure, and drying, so as to obtain the beautyberry total glycosides extract.

7. The preparation method according to the technical solution 6, wherein in the step (1), the extraction method is selected from a flash extraction method, a reflux extraction method, a microwave extraction method, an ultrasonic extraction method and a percolation extraction method.

8. The preparation method according to the technical solution 6 or 7, wherein in the step (3a), the resin filler is selected from a macroporous adsorbent resin, a polyamide resin and an ion exchange resin.

9. The preparation method according to any one of the technical solutions 6 to 8, wherein in the step (3a), the macroporous adsorbent resin filler is a macroporous adsorbent resin of the type HPD100, HPD200, D101, AB-8, SP825, ADS-7, and the like.

10. The preparation method according to any one of the technical solutions 6 to 9, wherein in the step (3a), the dilute alcohol aqueous solution is a 0 to 15 vol % dilute alcohol aqueous solution.

11. The preparation method according to anyone of the technical solutions 6 to 10, wherein in the step (3a), the high-concentration alcohol aqueous solution is a 30% to 90 vol % alcohol aqueous solution.

12. The preparation method according to anyone of the technical solutions 6 to 11, wherein in the step (3b), the organic solvent is n-butanol or ethyl acetate.

13. The preparation method according to anyone of the technical solutions 6 to 12, wherein in the step (3a), the following operation is performed one or more times after the concentration of the eluent under reduced pressure: the concentrated solution is dissolved with water, allowed to pass through a chromatographic column packed with a resin filler, washed with water and/or a dilute alcohol aqueous solution to remove impurities, and then eluted with an alcohol aqueous solution at a higher concentration. The eluent is collected and concentrated under reduced pressure.

14. Use of the beautyberry total glycosides extract of any one of the technical solutions 1 to 5 in the preparation of food, health products or drugs for use in treatment or adjuvant treatment of neurodegenerative diseases.

15. Use of the beautyberry total glycosides extract of any one of the technical solutions 1 to 5 in the preparation of cosmetics, health products or drugs for use in treatment or adjuvant treatment of skin diseases.

16. The use of the technical solution 15, wherein the skin disease is eczema or dermatitis.

DESCRIPTION OF THE DRAWINGS

In FIGS. 1 and 2, the linear relationship is Y=16374*X+ 18.793, R=0.9997; wherein, Y axis is peak area, X axis is verbascoside concentration (mg/mL), and the Arenarioside concentration is calculated based on the standard of verbascoside.

DETAILED DESCRIPTION OF THE PREFERRED EMBODIMENTS

In one aspect, the present invention provides a beautyberry total glycosides extract, containing 18% to 45% verbascoside and 15% to 40% Arenarioside based on weight. The extract of the present invention is prepared from leaves (preferably dried leaves) of *Callicarpa cathayana* H.T. Chang or *Callicarpa formosana* Rolfe.

Verbascoside and Arenarioside have structural formulae as follows:

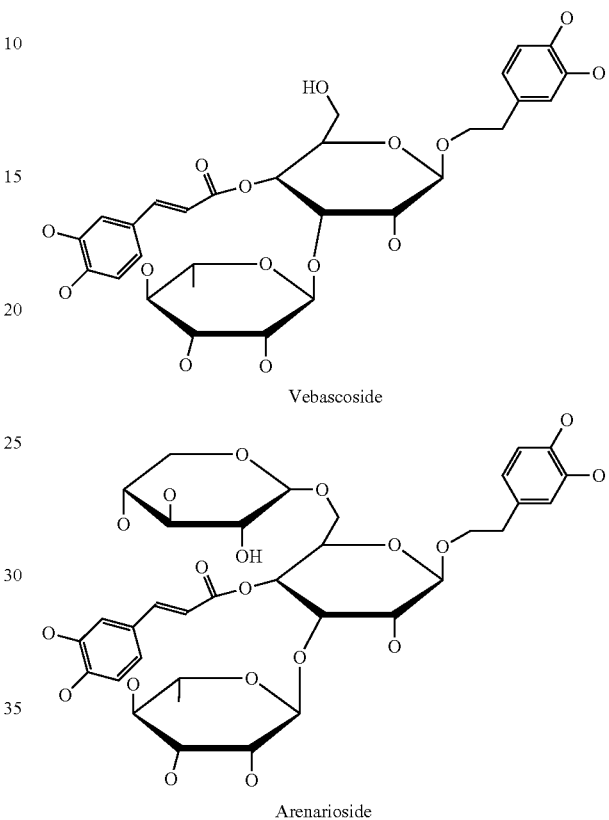

Vebascoside

Arenarioside

The concentration of verbascoside in the beautyberry extract of the present invention is 18% to 45%, preferably 28% to 45%, and preferably 28% to 38%, based on weight. The concentration of Arenarioside in the beautyberry extract of the present invention is 15% to 40%, preferably 24% to 40%, preferably 25% to 35%, and preferably 25% to 40%, based on weight.

The beautyberry extract of the present invention is extracted from *Callicarpa cathayana* H.T. Chang or *Callicarpa formosana* Rolfe.

*Callicarpa cathayana* H.T.Chang and *Callicarpa formosana* Rolfe are two relatively common species of *Callicarpa* plants with distribution in Guizhou, Zhejiang, Jiangxi, Fujian, Guangdong, Jiangsu, Hubei, Guangxi, Yunnan provinces and the like. Both species have large-scale cultivation, and are important sources of local revenue. Studies performed by the present inventors show that, the leaves of these two beautyberry species contain about 2% to 6% verbascoside and 1% to 4% Arenarioside.

The concentrations of phenylethanoid glycosides in different beautyberry medicinal materials are analyzed by the present inventors through the following chromatographic methods:

1. Preparation Method for the Test Samples:

0.25 g of powder (sieved through a gauge 3 screen) of dried leaves of a test beautyberry medicinal material is weighed precisely, into which is added 25 mL of a 70 (v/v) % methanol aqueous solution. The mixture is weighed, subjected to ultrasonic extraction for 20 min, then set cold, and compensated by a 70 (v/v) % methanol aqueous solution. The supernatant is taken, filtered, and the filtrate is taken for later use.

2. Chromatographic Condition:

Chromatographic column: a Cholester chromatographic column (4.6*250 mm, 5 μm); column temperature: 40° C.; detector: a UV-detector (for example, VWD or DAD); detection wavelength: 332 nm; flow rate: F=1.0 ml/min; sample amount: 10 μL;

mobile phase A: 0.1 (v/v) % formic acid—water, B: acetonitrile; elution gradient:

| Time (min) | A (v/v %) | B (v/v %) |
|---|---|---|
| 0 | 90 | 10 |
| 40 | 80 | 20 |
| 45 | 0 | 100 |
| 50 | 0 | 100 |

Figure 1:
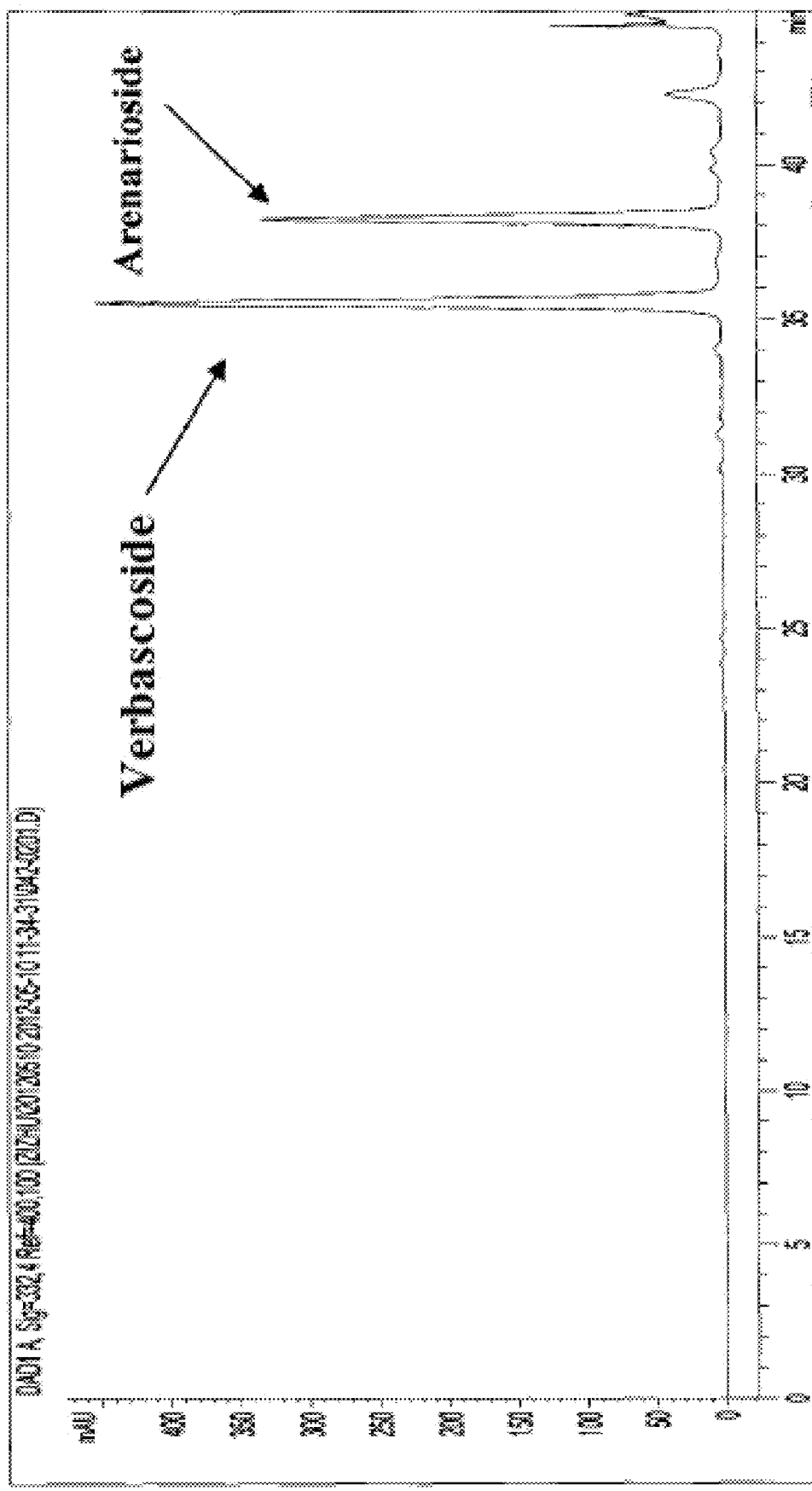
FIG. 1 is a typical high performance liquid chromatography (using a DAD detector) diagram of preparation method of the beautyberry total glycosides extract of the present invention from leaves of *Callicarpa cathayana* H.T. Chang.
Figure 2:
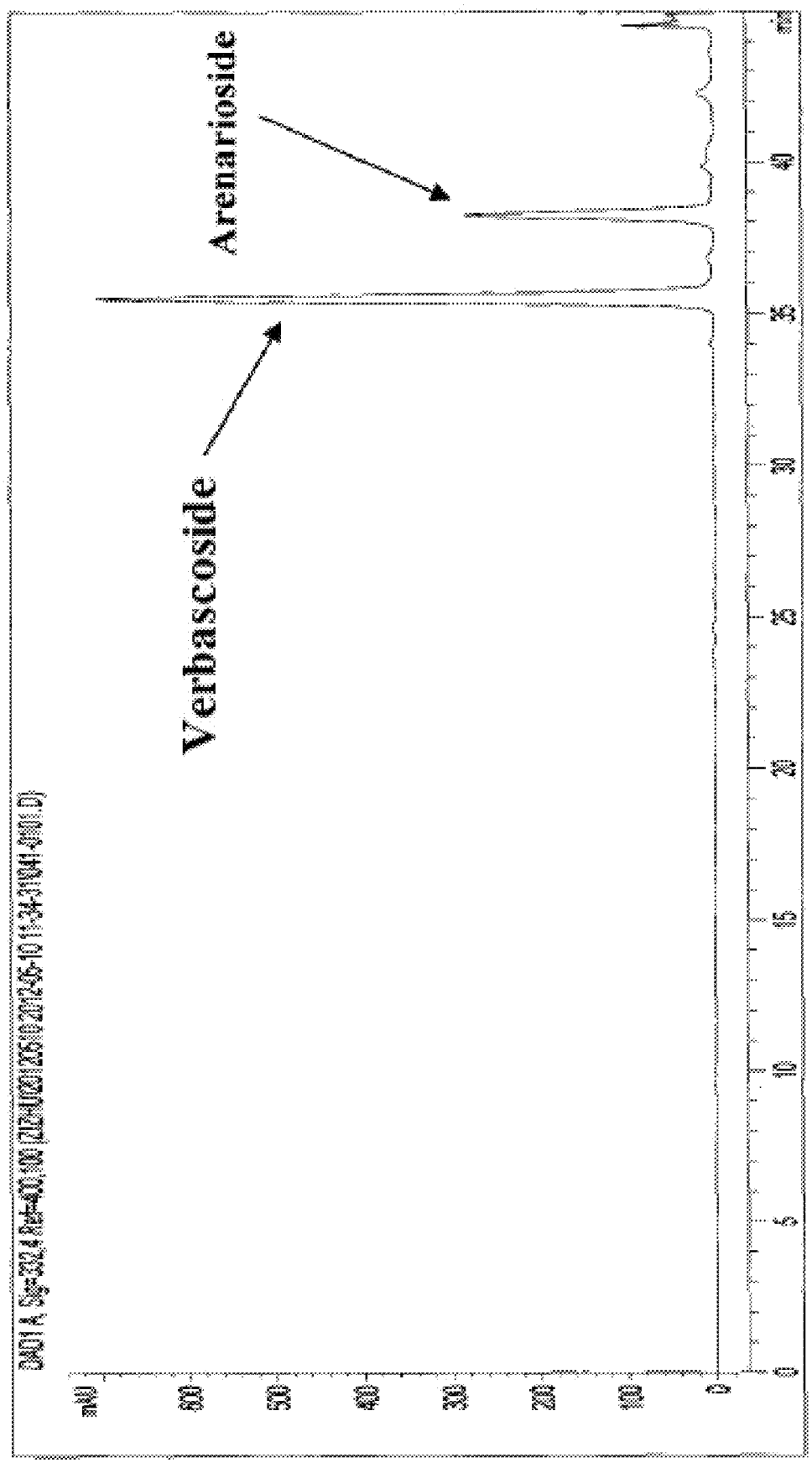
FIG. 2 is a typical high performance liquid chromatography (using a DAD detector) diagram of preparation method of the beautyberry total glycosides extract of the present invention from leaves of *Callicarpa formosana* Rolfe.

Typical HPLC (using the DAD detector) chromatograms of the beautyberry total glycosides extracts of the present invention from *Callicarpa cathayana* H.T.Chang leaves and *Callicarpa formosana* Rolfe leaves are seen in FIGS. 1 and 2.

Figure 6:
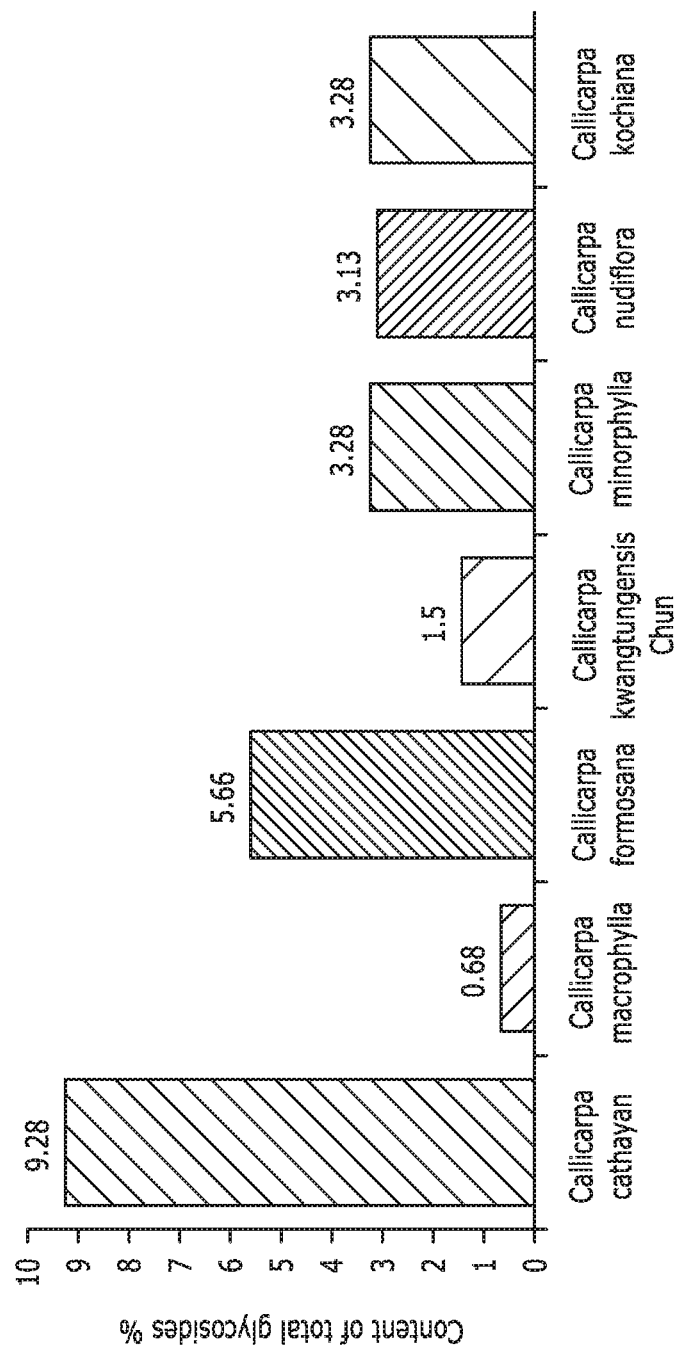
FIG. 6 shows example results of the Concentration of phenylethanoid glycosides in various species of beautyberry leaves.

Determination results of the concentration (based on weight) of phenylethanoid glycosides in various species of beautyberry leaves are seen in Table 1 and FIG. 6.

TABLE 1

Determination results of concentration of phenylethanoid glycosides in various species of beautyberry leaves

| Species of the medicinal material | Place of production | Poliumoside (%) | Forsythoside B (%) | Verbascoside (%) | Arenarioside (%) | Cocentration of total glycosides (%) |
|---|---|---|---|---|---|---|
| *Callicarpa cathayana* H. T. Chang | Guizhou | — | — | 4.96 | 4.32 | 9.28 |
| *Callicarpa macrophylla* | Hunan | — | — | 0.25 | 0.43 | 0.68 |
| *Callicarpa formosana* Rolfe | Guizhou | — | — | 3.64 | 2.02 | 5.66 |
| *Callicarpa kwangtungensis* Chun | Hunan | 0.68 | 0.52 | 0.30 | 0.00 | 1.50 |
| *Callicarpa minorphylla* | Jiangxi | — | — | 2.33 | 0.95 | 3.28 |
| *Callicarpa nudiflora* | Hainan | — | — | 3.07 | 0.06 | 3.13 |
| *Callicarpa kochiana* | Guangzhou | — | 2.2 | 1.08 | — | 3.28 |

As can be seen from Table 1 and FIG. 6 that, the *Callicarpa cathayana* H.T.Chang leaves and the *Callicarpa formosana* Rolfe leaves have rather high concentration of total glycosides (phenylethanoid glycosides), 3 to 15 times of that in other beautyberry species. Beautyberry medicinal materials with high concentrations brings tremendous convenience to enrichment of phenylethanoid glycosides.

Table 2 lists concentrations of phenylethanoid glycoside ingredients in different medicinal materials reported in the prior art.

TABLE 2

Reported concentrations of phenylethanoid glycoside ingredients in medicinal materials of different sources

| Medicinal material | Source | Index ingredient | Concentration reported in literatures (%) |
|---|---|---|---|
| *Callicarpa formosana* Rolfe[1] | Verbenaceae Callicarpa | Verbascoside | 0.73-1.36 |
| *Callicarpa macrophylla*[2] | Verbenaceae Callicarpa | Verbascoside | 0.22-1.38 |
| *Callicarpa nudiflora*[3] | Verbenaceae Callicarpa | Verbascoside | 0.04-0.43 |
| Broomrape[4] | Orobanchaceae Cistanche | Echinacoside | 0.024-3.13 |
| | | Verbascoside | 0.032-1.98 |
| Leaves of *Rehmannia glutinosa Libosch*[5] | Scrophulariaceae Rehmannia Libosch.ex Fisch. | Verbascoside | 0.40-2.62 |
| *Lamiophlomis rotata*[6] | Labiatae Lamiphlomis | Verbascoside | 0.02-0.80 |
| | | Forsythiaside B | 0.03-1.90 |
| *Chirita longgangensis* var. hongyao[7] | Gesneriaceae Chirita | Plantainoside D | 0.31-0.61 |
| | | Verbascoside | 0.41-0.67 |

TABLE 2-continued

Reported concentrations of phenylethanoid glycoside ingredients in medicinal materials of different sources

| Medicinal material | Source | Index ingredient | Concentration reported in literatures (%) |
|---|---|---|---|
| Caulis Akebiae[8] | Lardizabalaceae Akebia | Calceolarioside B | 0.02-0.80 |
| Phlomis umbrosa[9] | Labiatae Phlomis | Forsythiaside B | 1.00-1.30 |
|  |  | Verbascoside | 0.06-0.80 |
|  |  | Isoverbascoside | 0.01-0.03 |

[1]ZOU Guodong, CHENG Yanyang, FANG Tiezheng, et. al. HPLC determination of verbascoside in *Folium Callicarpae Pedunculatae*[J]. Chinese Journal of Pharmaceutical Analysis, 2010, 30 (1): 160-162;
[2]ZHOU Songyu, CHENG Yanyang, FANG Tiezheng. HPLC determination of verbascoside in *Callicarpa macrophylla*[J]. Chinese Journal of Pharmaceutical Analysis, 2010, 30 (10): 1295-1297
[3]LI Caitang, WEN Ping, GUO Qili, YU Jinbao. HPLC Determination of verbascoside in *Callicarpa nudiflora*[J]. Chinese Journal of Experimental Traditional Medicial Formulae, 2012, 18(1): 84-86
[4]ZHANG Heng, LI Xin, RENA·Kasimu, et. al. PR-HPLC determination of echinacoside and acteoside in broomrape from different hosts and different places of production[J]. Chinese Journal of Pharmaceutical Analysis, 2003, 4 (23): 254-257;
[5]BIAN Baolin, WANG Honghao, YANG Jian. Comparison of verbascoside content in 5 different medicinal materials[J]. China Journal of Chinese Materia Medica, 2010, 35 (6): 739-740
[6]PAN Zheng, GAO Yunling, ZHANG Tao, DENG Jie. HPLC determination of iridoid glycosides and phenylethanoid glycosides in rootsof *Lamiophlomis rotata*[J]. Chinese Traditional and Herbal Drugs, 2011, 42 (2): 279-281;
[7]WANG Manyuan, FAN Yuanjie, ZHANG Jing, GONG Muxin. Simultaneous determination of plantainoside D and verbascosidefrom stem of *Chirita longgangensisvar. hongyao* by RP-HPLC[J]. China Journal of Chinese Materia Medica, 2010, 35 (23): 3188-3191
[8]GAO Huimin, WANG Zhimin, QU Li, FU Xuetao, LI Lin. RP-HPLC Determination of calceolarioside B in *Caulis Akebiae* by RP-HPLC [J], China Journal of Chinese Materia Medica, 2007, 32 (6): 476-478;
[9]WANG Zheng, DENG Ruixue, YANG Youliang, et. al. HPLC simultaneous determination of three phenylethanoids in *Phlomis umbrosa*[J]. Chinese Journal of Pharmaceutical Analysis, 2011, 31 (4): 668-670

In another aspect, the present invention provides use of the beautyberry total glycosides extract of the present invention in the preparation of food, health products or drugs for use in treatment or adjuvant treatment of neurodegenerative diseases.

As demonstrated by the following examples, the beautyberry total glycosides extract of the present invention has a significant protective effect on nerve cells, has an evident ameliorative effect on the behavior disorder of Parkinson model mice and memory acquisition disorder of senile dementia model mice, and can effectively treat neurodegenerative diseases. The beautyberry total glycosides extract of the present invention can be combined with pharmaceutically acceptable auxiliary additives or food acceptable auxiliary additives, thereby to produce products for use in treatment or adjuvant treatment of neurodegenerative diseases, and the products may be food, health products or drugs, and the like. The products may be produced as granules, tablets, capsules, oral solutions, solid beverages, tea bags, powders and the like, as required.

In still another aspect, the present invention provides use of the beautyberry total glycosides extract of the present invention in the preparation of cosmetics, health products or drugs for use in treatment or adjuvant treatment of skin diseases. The skin diseases are selected from, but are not limited to dermatitis and eczema.

As demonstrated by the following examples, the beautyberry total glycosides extract of the present invention has positive effects in treatment and amelioration of dermatitis—eczema symptoms of DNCB induced mice. The beautyberry total glycosides extract can be used to effectively treat diseases, such as dermatitis or eczema related diseases. The beautyberry total glycosides extract of the this aspect can be combined with pharmaceutically acceptable or food and cosmetics acceptable auxiliary additives, thereby to produce products for external use in treatment and/or amelioration of dermatitis or eczema diseases, and the products may be cosmetics, health products, and drugs, and the like. The products may be produced as tinctures, creams, gels, patches, embrocations, sprays and the like, as required.

The pharmaceutically acceptable auxiliary additives, or food and cosmetics acceptable auxiliary additives suitable for use in the composition of the present invention include, but are not limited to binders, lubricants, disintegrating agents, flavoring agents, antioxidants, emulsifying agents, thickening agents, preservatives and the like.

The above binders include, but are not limited to hydroxy propyl cellulose, corn starch, pregelatinized starch, modified corn starch, polyvinyl pyrrolidone, hydroxypropyl methylcellulose, lactose, acacia, ethyl cellulose, cellulose acetate and the like.

The above lubricants include, but are not limited to magnesium stearate, zinc stearate, calcium stearate, talc, stearic acid, colloidal silicon dioxide, palmitinic acid and the like.

The above disintegrating agents include, but are not limited to crosslinked sodium carboxymethyl cellulose, crosslinked polyethylene pyrrolidone, starch, potato starch, pregelatinized starch, corn starch, sodium strach glycollate, microcrystalline cellulose, hydroxy propyl cellulose and the like.

The above flavoring agents include, but are not limited to fruit essence, aspartame, stevioside and the like.

The above antioxidants include, but are not limited to butylated hydroxyanisole (BHA), butylated hydroxytoluene (BHT), propyl gallate (PG), ascorbic acid, alpha-tocopherol and the like.

The above emulsifying agents include, but are not limited to acacia, sodium alkyl benzene sulfonate, sodium stearoyl lactylate and the like.

The above thickening agents include, but are not limited to methylcellulose, carboxyl methyl cellulose, hydroxy propyl cellulose, agar, sodium alginate, gelatin and the like.

The above preservatives include, but are not limited to potassium sorbate, sodium benzoate, Nipagin esters and the like.

In another aspect, the present invention provides a preparation method of the beautyberry total glycosides extract. The beautyberry total glycosides extract of the present invention is prepared from *Callicarpa cathayana* H.T. Chang leaves and *Callicarpa formosana* Rolfe leaves, by a method of water extraction, or alcohol extraction, or water-alcohol mixture extraction. Particularly, the present invention provides a preparation method of the beautyberry total glycosides extract, including the following steps:

(1) pulverizing leaves of *Callicarpa cathayana* H.T.Chang or *Callicarpa formosana* Rolfe, and extracting with a solvent 1 to 3 times, wherein the solvent is water, alcohol, or a mixture of water and alcohol;

(2) combining extract liquors from each extraction, concentrating under reduced pressure to remove the solvent in step (1); adding therein water in an amount of 0.5 to 2-time volume, standing overnight, centrifugating or filtering to obtain supernatant; and (3a) passing the supernatant through a chromatographic column packed with a resin filler, washing with water and/or a dilute alcohol aqueous solution to remove impurities, then eluting with an alcohol aqueous solution at a higher concentration, collecting eluent, concentrating under reduced pressure, and drying, so as to obtain the beautyberry total glycosides extract; or (3b) extracting the supernatant with an organic solvent, concentrating the organic phase under reduced pressure, and drying, so as to obtain the beautyberry total glycosides extract.

In the above method, the extraction method in the step (1) is selected from a flash extraction method, a reflux extraction method, a microwave extraction method, an ultrasonic extraction method and a percolation extraction method, preferably a flash extraction method, a reflux extraction method, or a percolation extraction method, and more preferably a flash extraction method.

In the above method, the leaves of *Callicarpa cathayana* H.T.Chang or *Callicarpa formosana* Rolfe in the step (1) are preferably dried leaves. Generally, the leaves of *Callicarpa cathayana* H.T.Chang or *Callicarpa formosana* Rolfe are pulverized into coarse powder or the coarsest powder as defined in general notices of "Chinese Pharmacopoeia (Version 2010)".

In the above method, alcohol in the step (1) is preferably ethanol or methanol, most preferably ethanol, preferably a 60% to 90 vol % alcohol aqueous solution, more preferably a 60% to 90 vol % ethanol or methanol aqueous solution.

In the above method, the solvent in the step (1) is used in an amount of 5 to 20 times the amount of the medicinal material (i.e., 5 to 20 ml of the solvent/g of the medicinal material), preferably in an amount of 8 to 12 times the amount of the medicinal material (i.e., 8 to 12 ml of the solvent/g of the medicinal material).

In the above method, in the step (3a), optionally the following operation is performed one or more times after the concentration of the eluent under reduced pressure: the concentrated solution is dissolved with water, allowed to pass through a chromatographic column packed with a resin filler, washed with water and/or a dilute alcohol aqueous solution to remove impurities, and then eluted with an alcohol aqueous solution at a higher concentration. The eluent is collected and concentrated under reduced pressure.

In the above method, the resin filler in the step (3a) is selected from, but is not limited to a macroporous adsorbent resin, a polyamide resin and an ion exchange resin. In an embodiment, the resin filler is preferably a macroporous adsorbent resin of the type HPD100, HPD200, D101, AB-8, SP825, or ADS-7, more preferably a macroporous adsorbent resin of the type D101 or AB-8.

In the above method, the dilute alcohol aqueous solution in the step (3a) is a 0 to 15 vol % dilute alcohol aqueous solution, preferably 0 to 10 vol %, and is used in an amount of 3 to 8 times the volume of the resin column bed, preferably 6 times the volume of the resin column bed. The volume of the resin column bed is varied according to the amount of supernatant actually to be treated. For example, a ratio of the volume of the resin column bed to the volume of the supernatant to be treated may be about 1:0.5 to 2. In an embodiment, the alcohol is preferably ethanol or methanol, most preferably ethanol.

In the above method, the alcohol aqueous solution at a higher concentration in the step (3a) is a 30% to 90 vol % alcohol aqueous solution, preferably a 30 to 50 vol % alcohol aqueous solution, more preferably a 30 to 40 vol % alcohol aqueous solution, and is used in an amount of 2 to 6 times the volume of the resin column bed, preferably 3 to 4 times the volume of the resin column bed. The volume of the resin column bed is varied according to the amount of supernatant actually to be treated. For example, a ratio of the volume of the resin column bed to the volume of the supernatant to be treated may be about 1:0.5 to 2. In an embodiment, the alcohol is preferably ethanol or methanol, most preferably ethanol.

In the above method, the organic solvent in the step (3b) is preferably n-butanol or ethyl acetate, and is used in an amount of 1 to 3 times, preferably 2 times the volume of the supernatant. In an embodiment, the organic solvent is a saturated n-butanol aqueous solution.

Beneficial Effects

The beautyberry total glycosides extract of the present invention contains high amounts of active ingredients, verbascoside and Arenarioside. The extract has a significant protective effect on nerve cells, has an evident ameliorative effect on the behavior disorder of Parkinson model mice and memory acquisition disorder of senile dementia model mice, and can be used to prepare food, health food or drugs for treatment or adjuvant treatment of neurodegenerative diseases. The beautyberry total glycosides extract of the present invention has good effects in treatment and amelioration of dermatitis—eczema symptoms of DNCB induced mice. The beautyberry total glycosides extract can effectively treat dermatitis or eczema related diseases, and can be used to prepare cosmetics, health products or drugs for external use in treatment or adjuvant treatment of skin diseases.

The beautyberry total glycosides extract provided by the present invention has a simple preparation process, is suitable for industrialized production, and has high yields of verbascoside and Arenarioside. The method of the present invention only employs water or alcohol as an extraction solvent, and the pollution is reduced. The resins employed are all renewable and recyclable, and the cost is low. The high-purity beautyberry total glycosides extract produced contains 18% to 45% (w/w) verbascoside and 15% to 40% Arenarioside (w/w). The process is stable, and the product quality is controllable.

EXAMPLES

The present invention will be illustrated below by means of examples, which however do not limit the present invention in any way.

In the following examples, *Callicarpa cathayana* H.T.Chang, *Callicarpa formosana* Rolfe and *Callicarpa minorphylla* were produced in Hubei province, and *Callicarpa nudiflora* was produced in Hainan province. Dried leaves of each medicinal material were pulverized into the coarsest powder (the definition thereof is seen in Chinese Pharmacopoeia, Version 2010, Part 2, General Notices). The flash extractor used in the extraction was a Model JHBE-50, and purchased from Jinnai Technology Development Co., LTD, Henan Province. Flash extraction was performed 2 times, each for 3 min. D101 and AB-8 macroporous adsorbent resins were both purchased from Baoen Chemical Co., LTD, Cangzhou city, Hebei Province. The polyamide resin (80 to 120 meshes) was purchased from Sinopharm Chemical Reagent Co., LTD.

Unless stated otherwise, the ethanol solution in the following examples refer to an ethanol aqueous solution, and is based on the percentage by volume.

Unless stated otherwise, in the following examples, the term "the volume of the concentrated solution was comparable to the amount of the medicinal material" means that the amount of the concentrated solution (in ml) was equal to the amount of the original medicinal material (in g); and the volume of the resin column bed was 2 to 0.5 times the volume of supernatant to be treated.

In the following examples, the centrifugation condition is 5000 rpm, for 10 minutes.

Example 1

Dried leaves of *Callicarpa cathayana* H.T. Chang were pulverized into the coarsest powder, and 90% ethanol was added therein in a 12-time amount (i.e., 12 ml per gram of the dried leaves of *Callicarpa cathayana* H.T.Chang). Flash extraction was performed for 3 min, and the extraction was performed twice. Extracts from the two extractions were combined, the extract liquor was concentrated under reduced pressure to remove ethanol, and the volume of the concentrated solution was comparable to the amount of the medicinal material. Water was added therein in an amount of 1-time volume, the mixture was stood overnight, and centrifugated to obtain supernatant. The supernatant was passed through a D101 macroporous adsorbent resin column, washed with water in an amount of 6 times the volume of the resin column bed, and then washed with 10% ethanol in an amount of 6 times the volume of the resin column bed. The aqueous washing solution and the 10% ethanol washing solution were discarded. Elution using 40% ethanol in an amount of 3 times the volume of the resin column bed was carried out, and eluent was collected. The eluent was concentrated under reduced pressure, to remove ethanol. The concentrated solution was diluted with water to an initial supernatant volume, then passed through a polyamide chromatographic column, and washed with water in an amount of 2 times the volume of the resin column bed. The aqueous washing solution was discarded. Then, elution using 30% ethanol in an amount of 3 times the volume of the resin column bed was carried out, and eluent was collected. The eluent was concentrated under reduced pressure, and dried, so as to obtain the beautyberry total glycosides extract.

Using *Callicarpa macrophylla*, *Callicarpa formosana* Rolfe, *Callicarpa minorphylla* or *Callicarpa nudiflora* in place of *Callicarpa cathayana* H.T.Chang as the raw medicinal material, respective beautyberry total glycosides extract was prepared according to the above method.

According to the HPLC determination method described above, the beautyberry total glycosides extracts of the above beautyberry medicinal materials of different sources were analyzed, with results as shown in Table 3:

TABLE 3

| Source of the medicinal material | Yield Y (%) | Verbascoside | | Arenarioside | | Beautyberry total glycosides extract Percentage-content (%) |
| --- | --- | --- | --- | --- | --- | --- |
| | | Percentage-content $P_i$ (%) | Recovery rate R (%) | Percentage-content $P_i$ (%) | Recovery rate R (%) | |
| *Callicarpa cathayana* H. T. Chang | 9.36 | 40.67 | 76.74 | 35.12 | 76.09 | 75.79 |
| *Callicarpa macrophylla* | 5.01 | 3.56 | 71.34 | 6.02 | 70.14 | 9.58 |
| *Callicarpa formosana* Rolfe | 7.94 | 35.17 | 76.71 | 19.25 | 75.66 | 57.96 |
| *Callicarpa minorphylla* | 9.51 | 17.25 | 70.41 | 7.23 | 72.38 | 24.48 |
| *Callicarpa nudiflora* | 8.77 | 24.36 | 69.59 | 0.49 | 71.62 | 24.85 |

In the above table, the yield (%) was calculated as follows:

$$Y = M_p/M_c \times 100$$

wherein $M_p$ is weight of the beautyberry total glycosides extract, and $M_c$ is weight of the medicinal material.

The recovery rate (%) was calculated as follows:

$$R = 100 \times (M_p \times P_i)/(M_c \times C_i)$$

wherein, $P_i$ is a perceage concentration of a certain ingredient i in the beautyberry total glycosides extract, $C_i$ is a percentage concentration of a certain ingredient i in the beautyberry medicinal material, $M_P$ is weight of the beautyberry total glycosides extract, and $M_C$ is weight of the beautyberry medicinal material.

As shown in Table 3, the beautyberry total glycosides extract prepared from *Callicarpa cathayana* H.T. Chang leaves or *Callicarpa formosana* Rolfe leaves has significantly higher concentrations of verbascoside and Arenarioside compared to that prepared from *Callicarpa macrophylla* leaves, *Callicarpa minorphylla* leaves and *Callicarpa nudiflora* leaves. In comparison with *Callicarpa macrophylla* leaves, *Callicarpa minorphylla* leaves and *Callicarpa nudiflora* leaves, the *Callicarpa cathayana* H.T. Chang leaves or *Callicarpa formosana* Rolfe leaves have a significantly higher concentration of the beautyberry total glycosides.

Example 2

Dried leaves of *Callicarpa formosana* Rolfe were pulverized into the coarsest powder, and 70% ethanol was added therein in a 12 times amount (i.e., 12 ml per gram of the dried leaves of *Callicarpa formosana* Rolfe). Flash extraction was performed for 3 min, and the extraction was performed twice. Extracts from the two extractions were combined, and the extract liquor was concentrated under reduced pressure to remove ethanol and to a volume of comparable to the amount of the medicinal material. Water was added therein in an amount of 1 time volume and the mixture was centrifugated to obtain supernatant after standing overnight. The supernatant was then passed through a D101 macroporous adsorbent resin column, and washed with water in an amount of 6 times the volume of the resin column bed. The aqueous washing solution was discarded. Elution using 30% ethanol in an amount of 4 times the volume of the resin column bed was carried out, and eluent was collected. The eluent was concentrated under reduced pressure, and dried, so as to obtain a beautyberry total glycosides extract. The composition of the extract was determined by the above HPLC method, with results shown in Table 4.

Example 3

Dried leaves of *Callicarpa cathayana* H.T.Chang were pulverized into the coarsest powder, and 90% ethanol was added therein in a 10 time amount (i.e., 10 ml per gram of the dried leaves of *Callicarpa cathayana* H.T.Chang). Decoction was performed under reflux (heated to boiling at atmospheric pressure) for 1 h, and the decoction was performed twice. Extract liquors from the two decoctions were combined, the extract liquor was concentrated under reduced pressure to remove ethanol, and the volume of the concentrated solution was comparable to the amount of the medicinal material. Water was added therein in an amount of 1 time the volume, the mixture was stood overnight, and centrifugated to obtain supernatant. The supernatant was passed through a D101 macroporous adsorbent resin column, washed with water in an amount of 3 times the volume of the resin column bed, and then washed with 10% ethanol in an amount of 3 times the volume of the resin column bed. The washing solution and the 10% ethanol washing solution were discarded. Then elution using 40% ethanol in an amount of 3 times the volume of the resin column bed was carried out, and eluent was collected. The eluent was concentrated under reduced pressure, and dried, so as to obtain a beautyberry total glycosides extract. The extract was analyzed by the above HPLC method, with results shown in Table 4.

Example 4

Dried leaves of *Callicarpa formosana* Rolfe were pulverized into the coarsest powder, and 70% ethanol was added therein in a 12-time amount (i.e., 12 ml per gram of the dried leaves of *Callicarpa formosana* Rolfe). Decoction was performed under reflux (heated to boiling at atmospheric pressure) for 1 h, and the decoction was performed twice. Extract liquors from the two decoctions were combined (please make sure), the extract liquor was concentrated under reduced pressure to remove ethanol, and the volume in milliliter of the concentrated solution was comparable to the amount of the medicinal material in gram. Water was added therein in an amount of 1 time volume, the mixture was stood overnight, and centrifugated to obtain supernatant. The supernatant was passed through an HPD100 macroporous adsorbent resin column, and washed with water in an amount of 6 times the volume of the resin column bed. The aqueous washing solution was discarded. Elution using 40% ethanol in an amount of 3 times the volume of the resin column bed was carried out, and eluent was collected. The eluent was concentrated under reduced pressure to remove ethanol. The concentrated solution was diluted with water to the initial supernatant volume, then passed through an ADS-7 resin column, and washed with water in an amount of 3 times the volume of the resin column bed. The aqueous washing solution was discarded. Then, elution using a 50% solution in an amount of 3 times the volume of the resin column bed was carried out, and eluent was collected. The eluent was concentrated under reduced pressure, and dried, so as to obtain a beautyberry total glycosides extract. The extract was determined by the above HPLC method, with results shown in Table 4.

Example 5

Dried leaves of *Callicarpa cathayana* H.T. Chang were pulverized into the coarsest powder, and subjected to percolation extraction for 10 h with 90% ethanol at a flow rate of 1 mL/h per gram of the coarse powder of *Callicarpa cathayana* H.T.Chang leaves. The decoction was collected and concentrated under reduced pressure to remove ethanol, and the volume of the concentrated solution was comparable to the amount of the medicinal material. Water was added therein in an amount of 1 time volume, and the mixture was let stood overnight and centrifugated to obtain supernatant. The supernatant was passed through a D101 macroporous adsorbent resin column, washed with water in an amount of 6 times the volume of the resin column bed to remove impurities, and then washed with 10% ethanol in an amount of 6 times the volume of the resin column bed. The aqueous washing solution and the 10% ethanol washing solution were discarded. Then elution using 40% ethanol in an amount of 3 times the volume of the resin column bed was carried out, and eluent was collected. The eluent was concentrated under reduced pressure, and dried, so as to obtain a beautyberry total glycosides extract. The extract was determined by the above HPLC method, with results shown in Table 4.

Example 6

Dried leaves of *Callicarpa cathayana* H.T. Chang were pulverized into coarse powder, and subjected to percolation extraction for 10 h with 90% ethanol at a flow rate of 1 mL/h per gram of the coarse powder of *Callicarpa cathayana* H.T. Chang leaves. The decoction was collected and concentrated under reduced pressure to remove ethanol, and the volume of the concentrated solution was comparable to the amount of the medicinal material. Water was added therein in an amount of 1 time volume, the mixture was let stood overnight, and centrifugated to obtain supernatant. The supernatant was passed through a D101 macroporous adsorbent resin column, washed with water in an amount of 6 times the volume of the resin column bed to remove impurities, and then washed with 10% ethanol in an amount of 6 times the volume of the resin column bed. The aqueous washing solution and the 10% ethanol washing solution were discarded. Then elution using 40% ethanol in an amount of 3 times the volume of the resin column bed was carried out, and eluent was collected. The eluent was concentrated under reduced pressure, to remove ethanol. The concentrated solution was diluted with water to an initial supernatant volume, then passed through a polyamide chromatographic column, and washed with water in an amount of 2 times the volume of the resin column bed. The aqueous washing solution was discarded. Then, elution with 30% ethanol in an amount of 3 times the volume of the resin column bed was carried out, and eluent was collected. The eluent was concentrated under reduced pressure, and dried, so as to obtain a beautyberry total glycosides extract. The extract was determined by the above HPLC method, with results shown in Table 4.

Example 7

Dried leaves of *Callicarpa cathayana* H.T. Chang were pulverized into the coarsest powder, and 90% ethanol was added therein in a 10-time amount (i.e., 10 ml per gram of the dried leaves of *Callicarpa cathayana* H.T. Chang). Decoction was performed under reflux (heated to boiling at atmospheric pressure) for 1 h, and the decoction was performed twice. Extracts from the two decoctions were combined, the extract liquor was concentrated under reduced pressure to remove ethanol, and the volume of the concentrated solution was comparable to the amount of the medicinal material. Water was added therein in an amount of 1 time volume, the mixture was let stood overnight, and centrifugated to obtain supernatant. A saturated n-butanol aqueous solution and an n-butyl alcohol solution in an equal volume were added into the supernatant for extraction twice. The n-butanol phases were combined, concentrated under reduced pressure, and dried, so as to obtain a beautyberry total glycosides extract. The extract was determined by the above HPLC method, with results shown in Table 4.

Example 8

Dried leaves of *Callicarpa cathayana* H.T. Chang were pulverized into the coarsest powder, and 90% ethanol was added therein in a 10-time amount (i.e., 10 ml per gram of the dried leaves of *Callicarpa cathayana* H.T.Chang). Decoction was performed under reflux (heated to boiling at atmospheric pressure) for 1 h, and the decoction was performed twice. Extract liquors from the two decoctions were combined, the extract liquor was concentrated under reduced pressure to remove ethanol, and the volume of the concentrated solution was comparable to the amount of the medicinal material. Water was added therein in an amount of 1 time volume, the mixture was stood overnight, and centrifugated to obtain supernatant. Ethyl acetate was added into the supernatant in an amount of 2 time volume, for extraction twice. The ethyl acetate phases were combined, concentrated under reduced pressure, and dried, so as to obtain a beautyberry total glycosides extract. The extract was determined by the above HPLC method, with results shown in Table 4.

Example 9

Protective effect of the beautyberry total glycosides extract of the present invention and related ingredients verbascoside and Arenarioside against MPP+ induced SH-SY5Y nerve cell injury 1. Instrument and Reagents A CO2 incubator, of model MCO-18AIC, purchased from SANYO Incorporation, Japan; a fully automated microplate reader, of model ELE800, purchased from Bio-tek Incorporation, U.S.A; a dynamic axial compression high pressure preparative liquid chromatograph, of model LC3000, 100 mm×650 mm (D×L), purchased from Beijing Chuangxin Tongheng Science and Technology Co., LTD; and C18 reversed phase chromatographic packing, 10 μm, purchased from Suzhou Sepax Technologies Co., LTD.

SH-SY5Y nerve cells were purchased from ATTC (American Type Culture Collection, Rockville, Md., U.S.A). The cells was cultured with RPMI1640 medium (a product of Hyclone Company) containing 10% fetal bovine serum, 2 mM/L glutamine, as well as 1% penicillium and streptomycin doubleantibiotics, in the incubator at 37° C. and 5% CO2.

MPP+ (1-methyl-4-phenylpyridine), MTT (thiazolyl blue), and DMSO (dimethyl sulfoxide) were all purchased from Sigma Company.

The phosphate buffer (PBS) was made immediately before use: 8 g NaCl, 0.2 g KCl, 1.44 g Na2HPO4, and 0.24 g KH2PO4 were dissolved with distilled water and then the solution was adjusted with HCl to a pH of 7.4. Water was added to a final volume of 1 L.

All other reagents were domestic chemically pure reagents.

2. Experimental Method 2.1 Preparation of Verbascoside and Arenarioside Monomers 20 g of the beautyberry total glycosides prepared in Example 6 was dissolved in 100 mL of water, and injected into the preparative liquid chromatographic column at a flow rate of 50 mL/min, with acetonitrile:water (0.1% TFA)=13:84 as a mobile phase. Isocratic elution was performe at a flow rate of 400 mL/min. On-line detection was performed

TABLE 4

Figure 3:
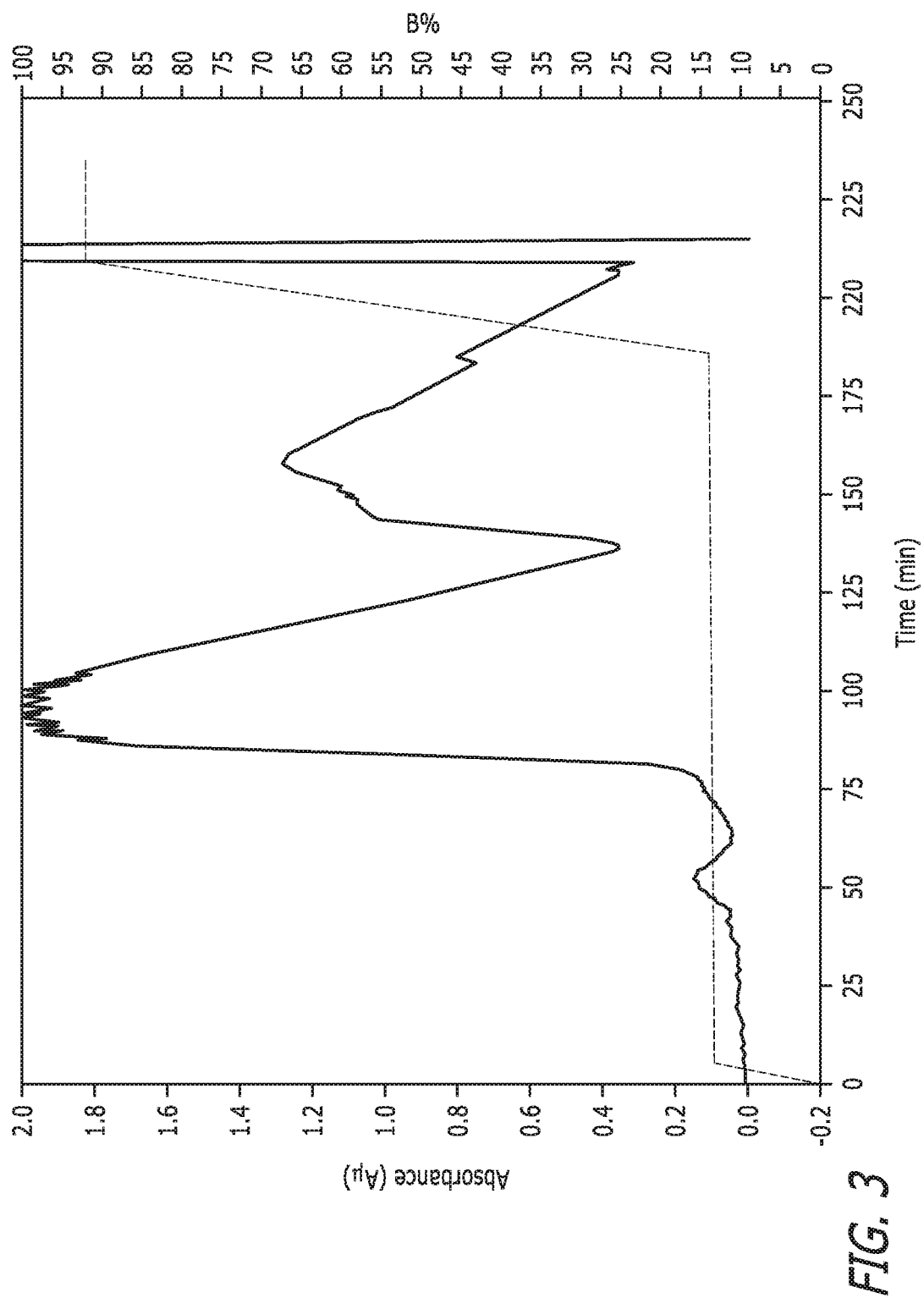
FIG. 3 shows a dynamic axial compression high pressure preparative liquid chromatogram.
Figure 4:
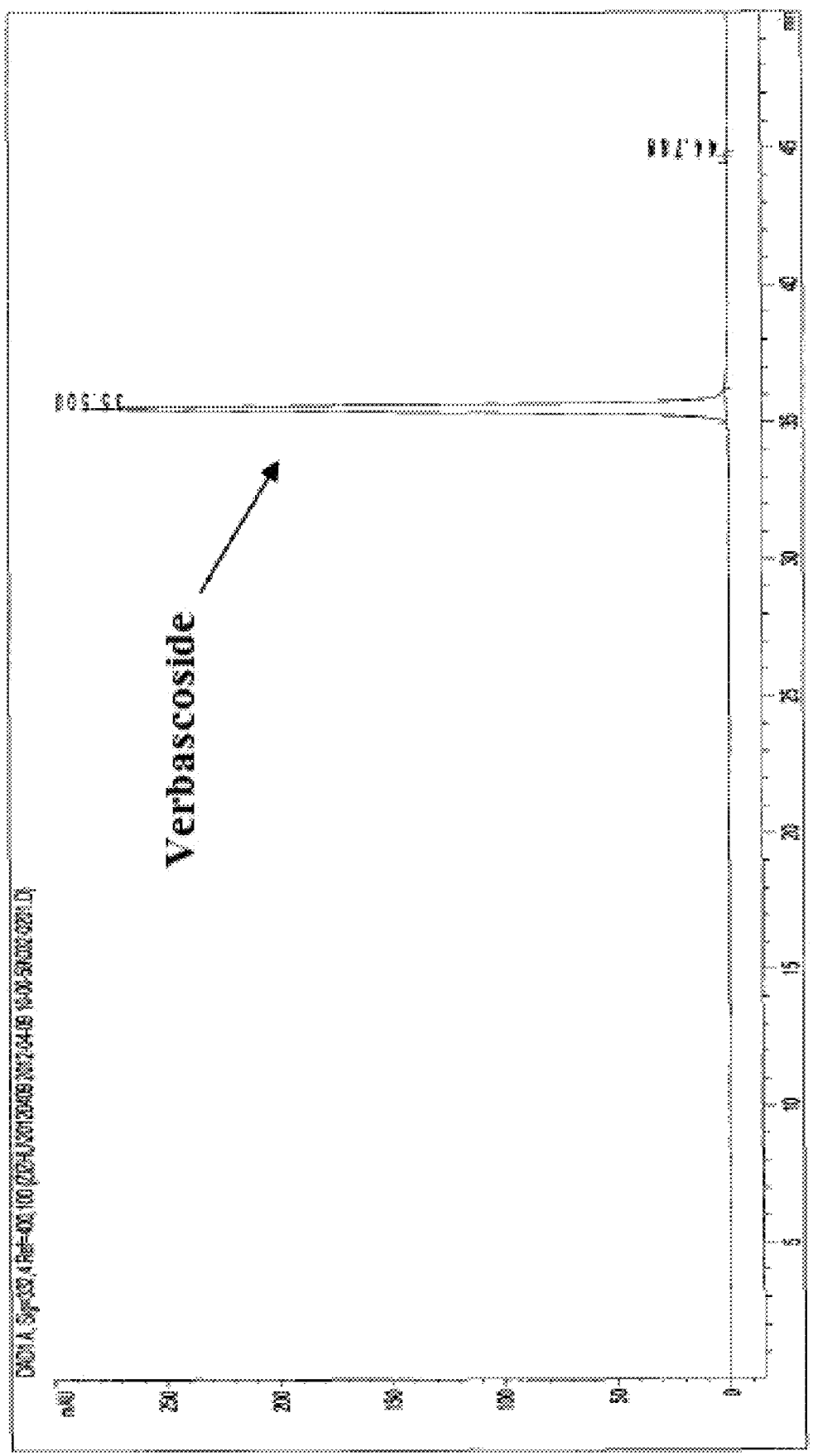
FIG. 4 shows a high pressure preparative liquid chromatogram of the verbascoside monomer.
Figure 5:
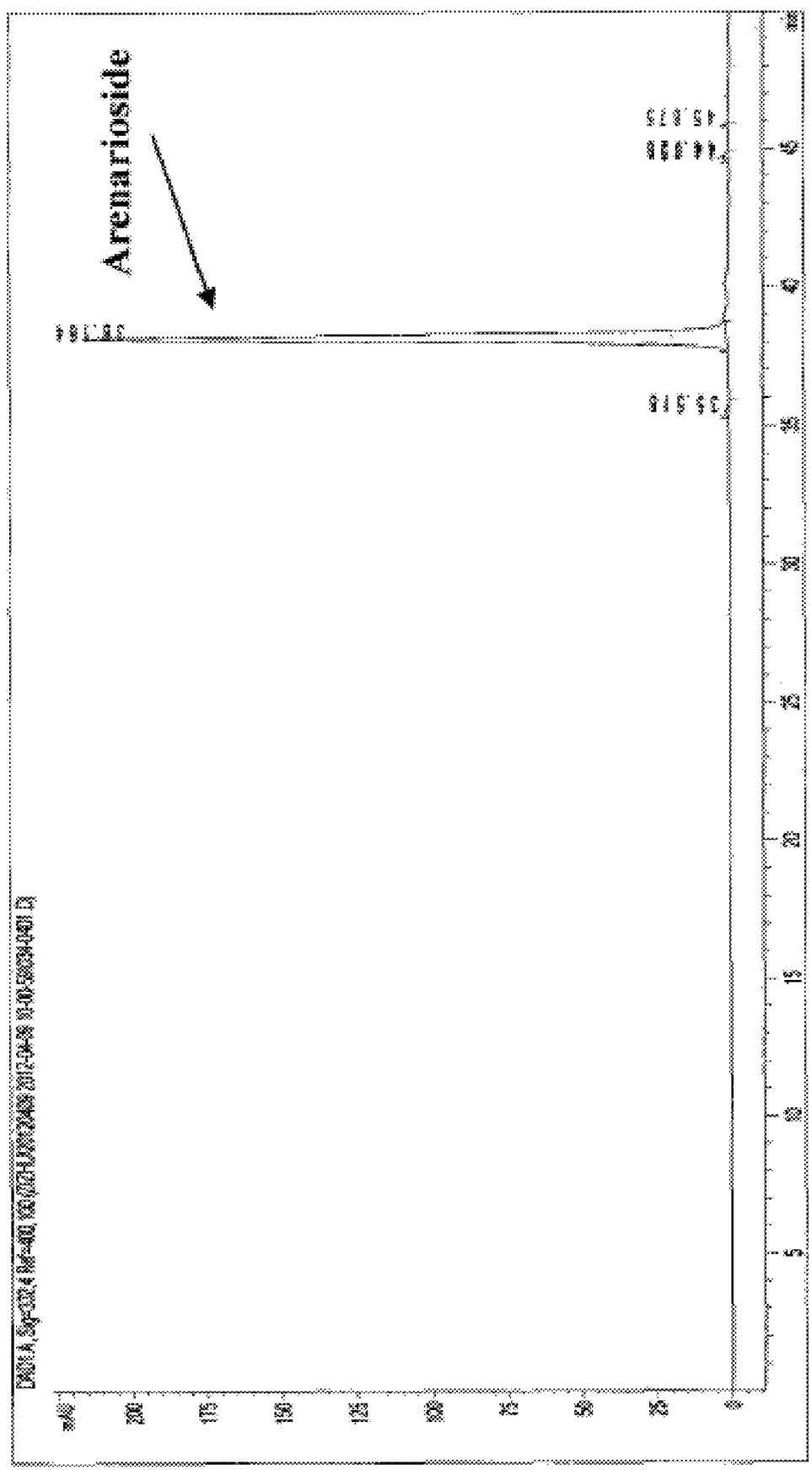
FIG. 5 shows a high pressure preparative liquid chromatogram of the Arenarioside monomer.

| Examples | Source of the medicinal material | Yield Y (%) | Verbascoside Concentration $P_i$ (%) | Verbascoside Recovery rate R (%) | Arenarioside Concentration $P_i$ (%) | Arenarioside Recovery rate R (%) |
|---|---|---|---|---|---|---|
| Example 1 | *Callicarpa cathayana* H. T. Chang | 9.36 | 40.67 | 76.74 | 35.12 | 76.09 |
| Example 1 | *Callicarpa formosana* Rolfe | 7.94 | 35.17 | 76.71 | 19.25 | 75.66 |
| Example 2 | *Callicarpa cathayana* H. T. Chang | 14.68 | 28.7 | 84.97 | 24.50 | 83.25 |
| Example 3 | *Callicarpa cathayana* H. T. Chang | 14.04 | 29.54 | 83.61 | 25.32 | 82.29 |
| Example 4 | *Callicarpa formosana* Rolfe | 7.86 | 33.12 | 71.51 | 18.29 | 71.16 |
| Example 5 | *Callicarpa cathayana* H. T. Chang | 10.01 | 37.75 | 76.18 | 28.01 | 64.90 |
| Example 6 | *Callicarpa cathayana* H. T. Chang | 8.32 | 45.06 | 75.58 | 40.25 | 77.51 |
| Example 7 | *Callicarpa cathayana* H. T. Chang | 21.32 | 18.12 | 77.89 | 15.34 | 75.70 |
| Example 8 | *Callicarpa cathayana* H. T. Chang | 19.64 | 19.23 | 76.14 | 15.95 | 72.51 | at 323 nm UV with the on-line chromatogram shiwn in FIG. 3. Fractions containing verbascoside and Arenarioside were collected respectively, concentrated under reduced pressure, and lyophilized, so as to obtain 4.52 g verbascoside and 3.68 gArenarioside. Purity of the two monomers was determined to be higher than 98%, and chromatograms of the two monomers are shown in FIGS. 4 and 5.

2.2 Protective Effect of the Beautyberry Total Glycosides Extract of the Present Invention Against MPP+ Induced SH-SY5Y Nerve Cell Injury The extract tested was the beautyberry total glycosides extract prepared in Example 5 which contained 37.75 wt % verbascoside and 28.01 wt % Arenarioside. The beautyberry total glycosides extract prepared in Example 5, and stock solutions of verbascoside and Arenarioside prepared in 2.1 above were dissolved and formulated respectively with phosphate buffer (PBS) and the resulted solutions were diluted to test concentrations with RPMI 1640 culture medium. MPP+ solution was prepared by dissolving MPP+ to 1 mM with PBS. The test concentration of MPP+ was 500 µM diluted with the culture medium. MTT was formulated with PBS, at a concentration of 0.5 mg/ml, and was filtered to remove bacteria using a 0.22 µm filter membrane prior to use.

SH-SY5Y nerve cells at a logarithmic growth phase were collected and counted with a cell counter. 200 µl of cell suspension with $4 \times 10^4$/ml was added into each well of the 96-well plate (converted to $8 \times 10^3$/200 µl of the culture medium) and was subjected to adherent culture in the incubator at 37° C. and 5% CO2 for 24 hours. The experiment included 11 groups: (1) a blank control group, wherein RPMI 1640 culture medium was used, and incubation at 5% CO2 and 37° C. was performed for 24 h; (2) a model group, wherein RPMI 1640 culture medium containing 500 µM MPP+ was used, and incubation at 5% CO2 and 37° C. was performed for 24 h; (3) a high dose group (16 µg/mL), a medium dose group (1.6 µg/mL), and a low dose group (0.16 µg/mL) (equivalent to 10 µM, 1 µM, and 0.1 µM verbascoside, respectively) of tests of the extract of Example 5 in the present invention; (4) a high dose group (10 µM), amedium dose group (1 µM), and a low dose group (0.1 µM) of theverbascoside monomer prepared above; and (5) a high dose group (10 µM), a medium dose group (1 µM), and a low dose group (0.1 µM) of the Arenarioside monomer prepared above; wherein, in each experimental dosage groups of (3), (4), and (5), mother liquid of the drug to be tested was firstly diluted to a set dosage concentration with the RPMI 1640 culture medium, then added at 100 µL into the cells, which were pre-protected at 5% CO2 and 37° C. for 24 h, then supernatant was carefully pipetted and discarded, then, mother liquid of the drug to be tested was diluted to a set dosage concentration with the RPMI 1640 culture medium containing 500 µM MPP+ that was formulated beforehand, then added at 100 µL into the cells, which were proceeded to incubation at 5% CO2 and 37° C. for 24 h. Supernatant was carefully pipetted and discarded, placed upside-down on an absorbent paper and patted dry. After the blank group and themodel group were incubated for 24 h, operations were performed using the same method. 5 parallel wells were provided for each group of the samples. MTT at a concentration of 0.5 mg/ml was added into each well of each group above, and incubated at 5% CO2 and 37° C. for 4 h. Supernatant was carefully pipetted and discarded, placed upside-down on an absorbent paper and patted dry. 200 µL of dimethyl sulfoxide (DMSO) was added into each well, and shaken for 300 s. The absorbance value of each well was determined at OD 570 nm, and cell viability was calculated according to the following formula:

$$\text{Cell viability} = \frac{\text{Sample group } OD_{570}}{\text{Blank group } OD_{570}} \times 100\%$$

Statistical treatment: all data were expressed as mean±standard deviation) ($\bar{x} \pm s$), comparison among groups was carried out by T-test, and significance of the difference was determined by variance analysis (if $p<0.05$, there is difference, and if $P<0.01$, there is significant difference).

3. Experimental Results

Figure 7:
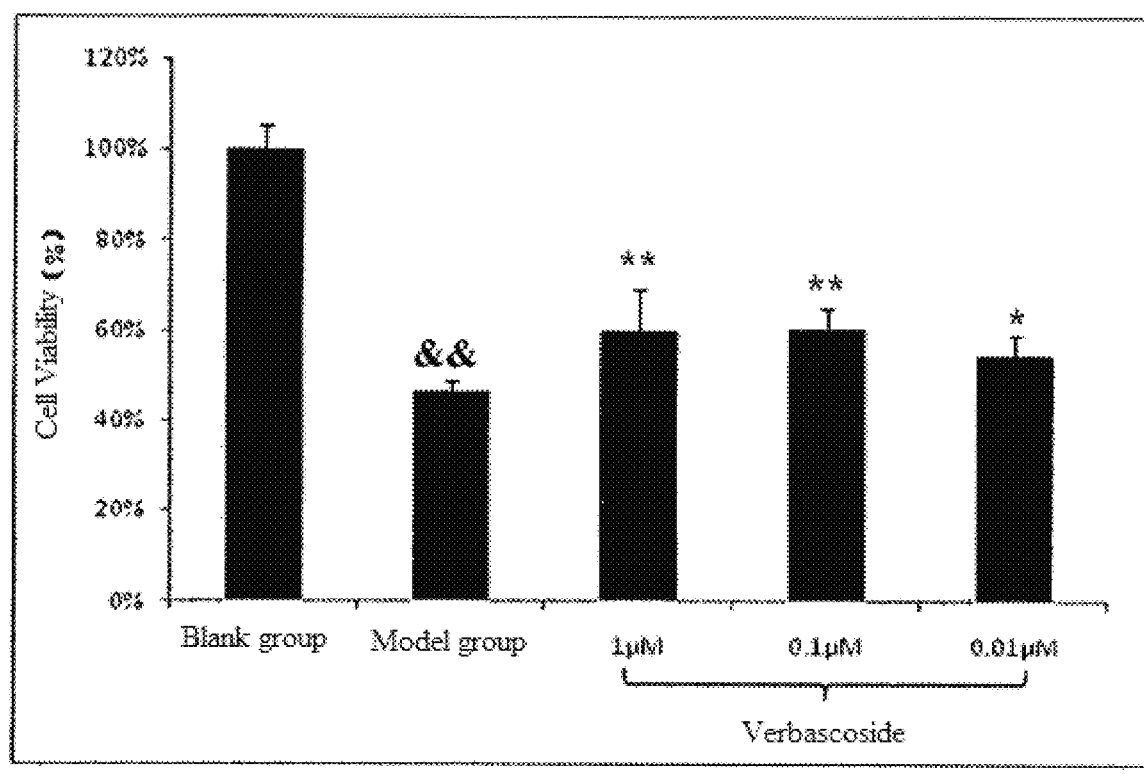
FIG. 7 shows the protective effect of various concentrations of verbascoside on MPP$^+$ induced SH-SY5Y nerve cell injury, wherein "&&" denotes P<0.01 as compared with a blank control group, "*" denotes p<0.05 as compared with a model group, and "**" denotes p<0.01 as compared with the model group.

As shown in FIG. 7, the verbascoside monomer has a protective effect against $MPP^+$ induced SH-SY5Y nerve cell injury, as the verbascoside groups of 0.1 µM and 1 µM both have significant difference compared to the model group ($p<0.01$).

Figure 8:
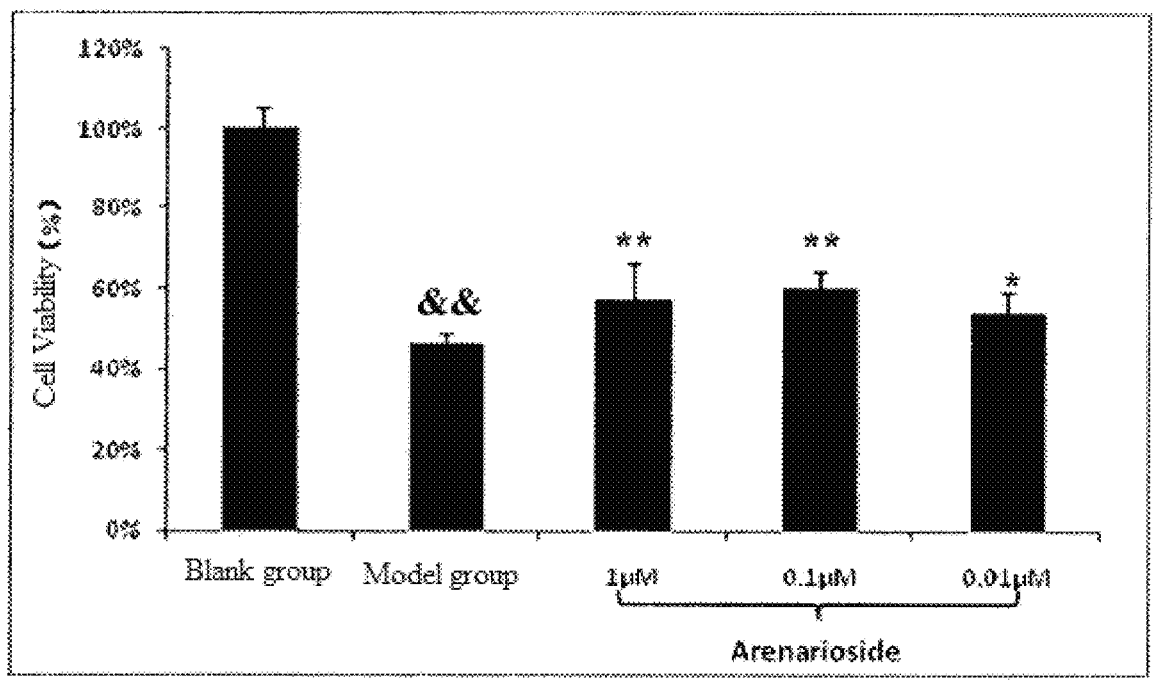
FIG. 8 shows the protective effect of various concentrations of Arenarioside on MPP$^+$ induced SH-SY5Y nerve cell injury, wherein "&&" denotes P<0.01 as compared with a blank control group, "*" denotes p<0.05 as compared with a model group, and "**" denotes p<0.01 as compared with the model group.

As shown in FIG. 8, the Arenarioside monomer has a protective effect against $MPP^+$ induced SH-SY5Y nerve cell injury, wherein the Arenarioside groups at concentrations of 0.1 µM and 1 µM both have significant higher cell viability as compared with the model group ($p<0.01$).

Figure 9:
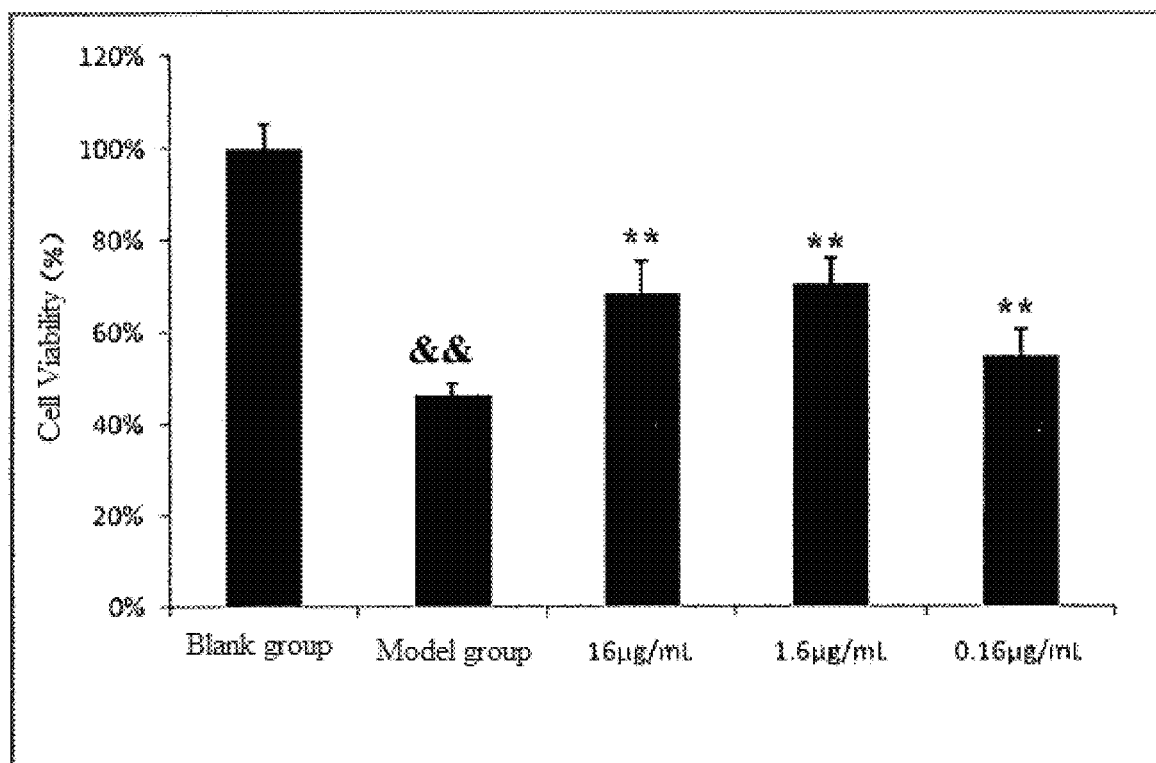
FIG. 9 shows the protective effect of various concentrations of the beautyberry total glycosides extract prepared in Example 5 of the present invention on MPP$^+$ induced SH-SY5Y nerve cell injury, wherein "&&" denotes P<0.01 as compared with a blank control group, "*" denotes p<0.05 as compared with a model group, and "**" denotes p<0.01 as compared with the model group.

As can be known from FIG. 9, the beautyberry total glycosides extract prepared in Example 5 of the present invention has a protective effect against $MPP^+$ induced SH-SY5Y nerve cell injury, extract groups of the present invention at three concentrations, i.e., high, medium, and low concentrations all have significant difference as compared with the model group ($p<0.01$).

Example 10

Protective effect of the beautyberry total glycosides extract of the present invention against $MPP^+$ induced SH-SY5Y nerve cell injury 1. Instrument and Reagents Instrument and reagents were the same as those in Example 9, except that no verbascoside monomer or Arenarioside monomer was used.

2. Experimental Method

The extracts tested were beautyberry total glycosides extracts prepared in Examples 4, 6 and 7 which contained 33.12 wt %, 45.06 wt % and 18.12 wt % verbascoside respectively, and 18.29 wt %, 40.25 wt % and 15.34 wt % Arenarioside respectively.

The experiment included 8 treatment groups: (1) a blank control group, wherein RPMI 1640 culture medium was used, and incubation at 5% $CO_2$ and 37° C. was performed for 24 h; (2) a model group, wherein RPMI 1640 culture medium containing 500 µM $MPP^+$ was used, and incubation at 5% $CO_2$ and 37° C. was performed for 24 h; and(3) a high dose group (16 µg/mL) and a low dose group (1.6 µg/mL) of the beautyberry total glycosides extracts prepared in Examples 4, 6 and 7 of the present invention. The treatment method was similar to that in Example 9.

Experimental Results

Figure 10:
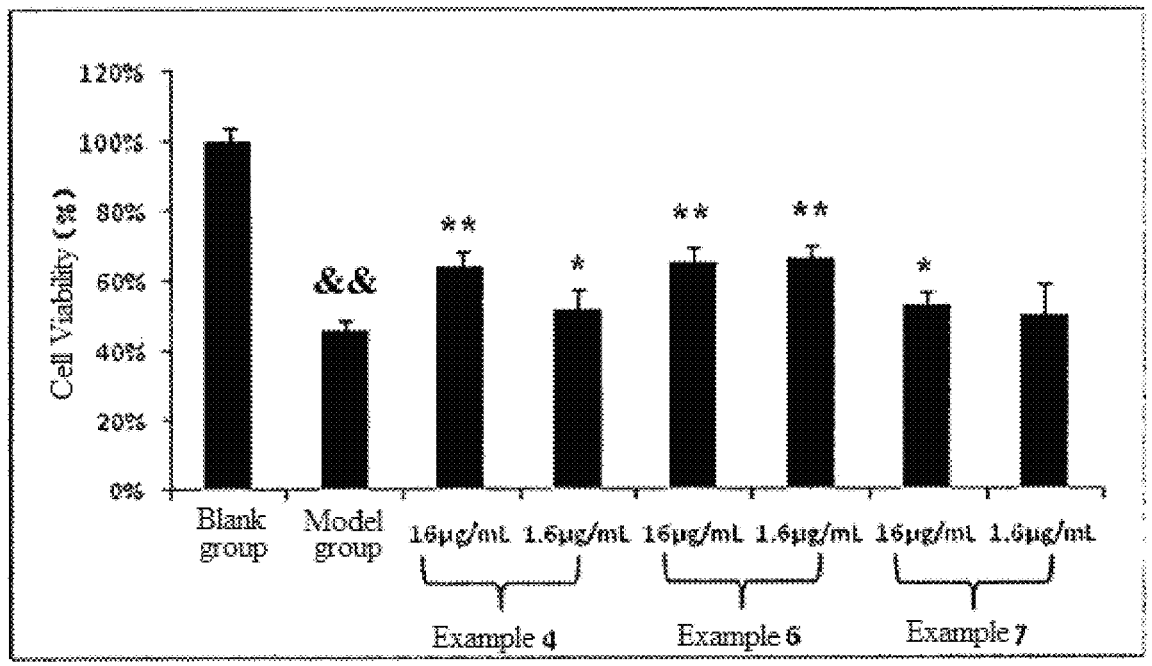
FIG. 10 shows the protective effect of various concentrations of the beautyberry total glycosides extracts prepared in Examples 4, 6 and 7 of the present invention on MPP$^+$ induced SH-SY5Y nerve cell injury, wherein "&&" denotes P<0.01 as compared with a blank control group, "*" denotes p<0.05 as compared with a model group, and "**" denotes p<0.01 as compared with the model group.

As shown in FIG. 10, the beautyberry total glycosides extract prepared by the present invention has a protective effect against $MPP^+$ induced SH-SY5Y nerve cell injury. The high dose group (16 µg/mL) of the beautyberry total glycosides extract prepared in Example 4 has significant higher cell viability compared to the model group ($p<0.01$). The low dose group (1.6 µg/mL) of the beautyberry total glycosides extract prepared in Example 4 has also higher cell viability compared with the model group ($p<0.05$). The high dose group (16 μg/mL) and the low dose group (1.6 μg/mL) of the beautyberry total glycosides extracts prepared in Example 6 both have significant difference as compared with the model group (p<0.01). Whereas the high dose group (16 μg/mL) of the beautyberry total glycosides extract prepared in Example 7 has difference as compared with the model group (p<0.05). The low dose group (1.6 μg/mL) of the beautyberry total glycosides extract prepared in Example 7 has no statistical difference as compared with the model group.

Example 11

Effects of the beautyberry total glycosides extract of the present invention on MPTP induced Parkinson mice model 1. Material and Method 1.1 Animal Animals were male Kunming mice of 7-week age, with body weight of 18 to 22 g, supplied by Shanghai Slaccas Experimental Animal Limited Liability Company. Certification number: 2007000539123.

1.2 Drug and Reagent

The extracts prepared in Examples 6 and 7 were tested as the beautyberry total glycosides extracts of the present invention, wherein the beautyberry extract obtained in Example 6 contained 45.06 wt % verbascoside and 40.25 wt % Arenarioside, and the beautyberry extract obtained in Example 7 contained 18.1 wt % verbascoside and 15.34 wt % Arenarioside. MPTP (1-methyl-4-phenyl-1,2,3,6-tetrahydropyridine) was purchased from Sigma Company. Broomrape total glycosides were prepared according to the preparation method 2 in particular embodiments of Chinese patent application No. CN200710040195.2, and contained 28.23 wt % echinacoside, 4.18 wt % verbascoside, and 5.30 wt % isoverbascoside. The above extracts were formulated into solution at a concentration of 10 to 30 mg/mL with normal saline.

1.3 Instrument

A mouse spontaneous activity recorder of model YLS-1A, purchased from Shanghai Xinman Science and Education Equipment Co., LTD, and a mouse rotating drum motion tester of model RB-200B, purchased from Beijing Xintiandi Science and Technology Company.

2. Establishment of Animal Model and Group Dosage 70 mice were randomly divided into 7 groups which included a blank control group without MPTP treatment, a model group, a broomrape total glycoside group (400 mg/kg), a high dose group (300 mg/kg) and a low dose group (100 mg/kg) of the beautyberry total glycosides extract of Example 6 of the present invention, a high dose group (300 mg/kg) and a low dose group (100 mg/kg) of the beautyberry total glycosides extract of Example 7 of the present invention, respectively. According to the above dose arrangement, each drug test group was continuously dosed by gastric lavage for 14 days, 0.25 mL each time. The animals in model group and all groups with extract treatment were intraperitoneally injected with 0.25 mL of MPEP (0.25 mg/kg) on the 11th, 12th, 12th and 14th day of dosing. Measurements of of behavior of animals were carried out 1 day after the last dosage.

3. Measurements 3.1 General Observation

General behavior and performance after modeling of the intraperitoneal injection of MPTP in the mice were observed for any abnormal responses, and differences among the groups were compared and analyzed.

3.2 Experiment of Spontaneous Activity

Spontaneous activities of the mice in each of the experimental groups were determined using the mouse spontaneous activity recorder of model YLS-1A. The mice were placed into spontaneous activity boxes (5 mice were determined simultaneously each time, with 1 mouse in each activity box) and recorded for the mice activity automatically with the recorder to determine the activity frequency of each mouse within 5 min, and statistical treatment was carried out.

3.3 Rotating Drum Experiment

Rotating drum behavior and performance of the mice in each experimental group were tested using the mouse rotating drum motion tester of model RB-200B. Before the test, the mice were trained continuously for 3 days, twice every day, at a rotation rate of 12 r/min, for a training time of 120 s. The mice were placed onto a rotating drum at a rotation rate of 35 r/min. The length of time a mouse could stay on the rotating drum is considered as the motor latency of the mouse. Each mouse was measured 3 times.

Statistical treatment: all data were expressed as mean±standard deviation ($\bar{x}$±s), comparison among groups was carried out by T-test, and significance of the difference was determined by variance analysis (if p<0.05, there is difference, and if P<0.01, there is significant difference).

4. Results 4.1 General Observation 5 min after the MPTP injection, mice with MPTP treatments showed abnormal general behavior and performance as compared with the blank control. Abnormities of these mice include erect tail, erect hair, increased salivary secretion, accelerated breathing, muscular hypotonus, sensitivity to environmental stimulation, dental tremor, and the like, with duration of generally 3 to 4 h. However, mice in the high dose group (300 mg/kg) and the low dose group (100 mg/kg) of the beautyberry total glycosides extracts of Examples 6 and 7 in the present invention and in the broomrape total glycoside group (400 mg/kg) showed significantly reduced symptoms of erect tail, erect hair, increased salivary secretion, accelerated breathing, muscular hypotonus, sensitivity to environmental stimulation, dental tremor, and the like. Moreover the duration of abnormities appeared on mice of these groups was about 1 h, shorter than those in MMTP only group.

4.2 Experiment of Spontaneous Activity

Figure 11:
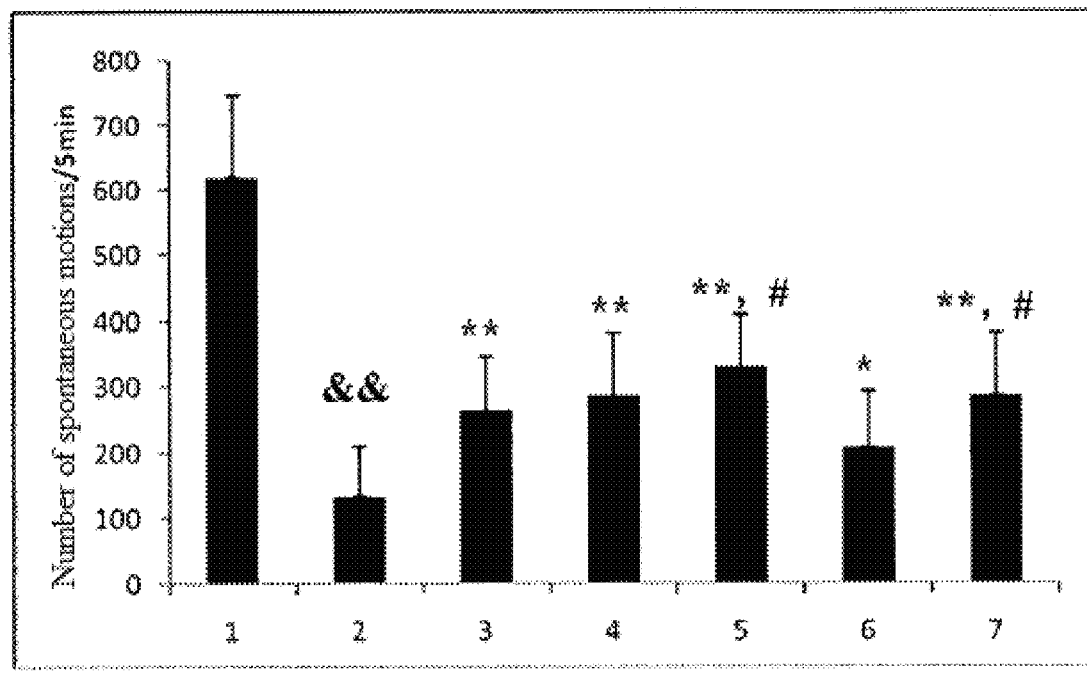
FIG. 11 shows influence of the phenylethanoid glycoside extract on spontaneous activities of mice with MPTP induced Parkinson's disease, wherein 1: a blank control group; 2: a model group; 3: a broomrape total glycoside group (400 mg/kg); 4: a low dose group (100 mg/kg) of the beautyberry total glycosides extract of Example 6 of the present invention; 5: a high dose group (300 mg/kg) of the beautyberry total glycosides extract of Example 6 of the present invention; 6: a low dose group (100 mg/kg) of the beautyberry total glycosides extract of Example 7 of the present invention; 7: a high dose group (300 mg/kg) of the beautyberry total glycosides extract of Example 7 of the present invention; "&&" denotes P<0.01 as compared with the blank control group, "*" denotes p<0.05 as compared with the model group, "**" denotes p<0.01 as compared with the model group, and "#" denotes P<0.05 as compared with the broomrape total glycoside group.

As shown in FIG. 11, the MPTP model group hadsignificantly decreased activity frequency as compared with the blank control group (P<0.01). Groups with treatments of total broomrape glycosides and the beautyberry total glycosides extract of the present invention had increased activity frequency as compared with the model group. Wherein, the high dose group (300 mg/kg) and the low dose group (100 mg/kg) of the beautyberry total glycosides extracts of Example 6 in the present invention had significant more spontaneous activities compared with the model group (P<0.01). The group (300 mg/kg) of the high-concentration beautyberry total glycosides extract of Example 7 in the present invention had significant more spontaneous activities compared with the model group (P<0.01), whereas the group (100 mg/kg) of the low-concentration beautyberry total glycosides extract of Example 7 in the present invention had difference as compared with the model group (P<0.05). The groups (300 mg/kg) of the high-concentration beautyberry total glycosides extracts of Examples 6 and 7 in the present invention both had better effects and have difference compared to the broomrape group (400 mg/kg) (P<0.05).

4.3 Rotating Drum Experiment

Figure 12:
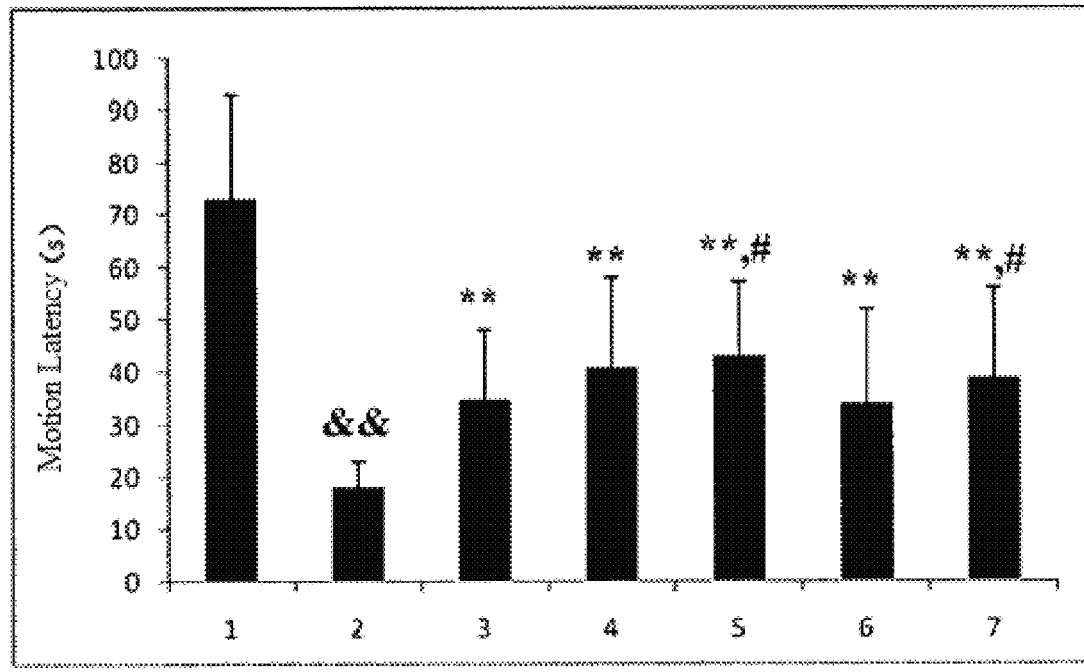
FIG. 12 shows influence of the phenylethanoid glycoside extract on the rotating drum behavior of mice with MPTP induced Parkinson's disease, wherein 1: a blank control group; 2: a model group; 3: a broomrape total glycoside group (400 mg/kg); 4: a low dose group (100 mg/kg) of the beautyberry total glycosides extract of Example 6 of the present invention; 5: a high dose group (300 mg/kg) of the beautyberry total glycosides extract of Example 6 of the present invention; 6: a low dose group (100 mg/kg) of the beautyberry total glycosides extract of Example 7 of the present invention; 7: a high dose group (300 mg/kg) of the beautyberry total glycosides extract of Example 7 of the present invention; "&&" denotes P<0.01 as compared with the blank control group, "*" denotes p<0.05 as compared with the model group, "**" denotes p<0.01 as compared with the model group, and "#" denotes P<0.05 as compared with the broomrape total glycoside group.

As shown in FIG. 12, the MPTP model group had significantly shortened motion latency compared to the blank control group (P<0.01). Groups or treatments of broomrape total glycosides and the beautyberry total glycosides extract of the present invention all had significantly increased rotating drum motion latency as compared with the model group (P<0.01). The groups (300 mg/kg) of the high-concentration beautyberry total glycosides extracts of Examples 6 and 7 in the present invention both had better effects and had difference (P<0.05) compared to the broomrape total glycoside group (400 mg/kg).

Example 12

Ameliorative effect of the beautyberry total glycosides extract of the present invention against scopolamine induced memory acquisition disorder in mice 1. Material and Method
   1.1 Animal Animals were male Kunming mice of 7-week age, with body weight of 18 to 22 g, supplied by Shanghai Slaccas Experimental Animal LimitedLiabilityCompany. Certification number: 2007000539123.

1.2 Drug and Reagent

The beautyberry total glycosides extracts prepared in Examples 6 and 7 were tested, wherein the beautyberry extract obtained in Example 6 contained 45.06 wt % verbascoside and 40.25 wt % Arenarioside, and the beautyberry extract obtained in Example 7 contained 18.1 wt % verbascoside and 15.34 wt % Arenarioside. The scopolamine hydrobromide injection solution was produced by Beijing Double-crane Pharmaceutical Company Limited by Shares. *Callicarpa kochiana* extracts were prepared according to the method of Example 1 in Chinese patent CN201010146367.6, and contained 47.25 wt % forsythiaside B, and 17.26 wt % verbascoside as analyzed by the HPLC method. The above extracts were formulated into a solution at a concentration of 10 to 30 mg/mL with normal saline.

1.3 Instrument

STT-2 MouseStep-Down instrument, purchased from Shanghai Xinman Science and Education Equipment Co., LTD.

2. Animal Grouping and Dosage 70 mice were randomly divided into 7 groups, which were a blank control group, a model group, a *Callicarpa kochiana* total glycosides group (300 mg/kg), a high dose group (300 mg/kg) and a low dose group (100 mg/kg) of the beautyberry total glycosides extract of Example 6 of the present invention, a high dose group (300 mg/kg) and a low dose group (100 mg/kg) of the beautyberry total glycosides extract of Example 7 of the present invention, respectively. Each drug test group was continuously dosed by gastric lavage for 30 days, 0.25 mL each time, and the blank control group and the model group were continuously dosed with an equal amount of normal saline by lavage for 30 days.

3. Establishment and Test of a Model of Scopolamine Induced Memory Acquisition Disorder in Mice Mice were trained 1 h after administration of drugs on the 29th day of the dosing perioed. At 15 min before the training, 1 mg/kg scopolamine was intraperitoneally injected into each animal in each experimental group except the blank control group and 1 mg/kg normal saline was intraperitoneally injected in the blank control group. For the training mice waere first placed into a response chamber of the step down instrument for environmental adaptation for 3 min. Then 36 V alternating current was switched on immediately. Most of the mice jumped on the elevated platform after subjecting to electric shock to escape from the electric shock, and mice that had jumped down from the jumping platform would jump again back onto the jumping platform upon electric shock. The training was lasted for 5 min. Test was performed after 24 h, i.e., the last day of the dosing period, wherein the mice were placed on the jumping platform, the time (latency T) when a mouse jumped down from the elevated platform for the first time, as well as the number (error number N) of electric shock experienced within 5 min were recorded.

Statistical treatment: all data were expressed as mean±standard deviation ($\bar{x}\pm s$), comparison among groups was carried out by T-test, and significance of the difference was determined by variance analysis (if p<0.05, there is difference, and if P<0.01, there is significant difference).

4. Results

Figure 13:
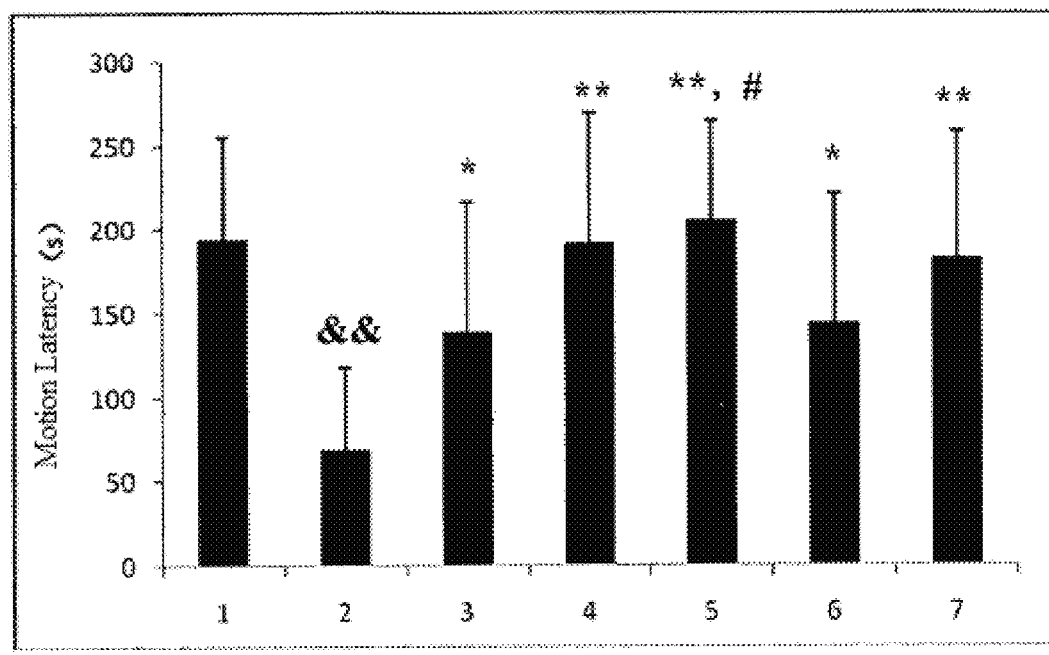
FIG. 13 shows influence of the beautyberry total glycosides extract on step down latency of scopolamine induced mice, wherein 1: a blank control group; 2: a model group; 3: a *Callicarpa kochiana* total glycosides group (300 mg/kg); 4: a low dose group (100 mg/kg) of the beautyberry total glycosides extract of Example 6 of the present invention; 5: a high dose group (300 mg/kg) of the beautyberry total glycosides extract of Example 6 of the present invention; 6: a low dose group (100 mg/kg) of the beautyberry total glycosides extract of Example 7 of the present invention; 7: a high dose group (300 mg/kg) of the beautyberry total glycosides extract of Example 7 of the present invention; "&&" denotes P<0.01 as compared with the blank control group, "*" denotes p<0.05 as compared with the model group, "**" denotes p<0.01 as compared with the model group, and "#" denotes P<0.05 as compared with the *Callicarpa kochiana* total glycosides group.
Figure 14:
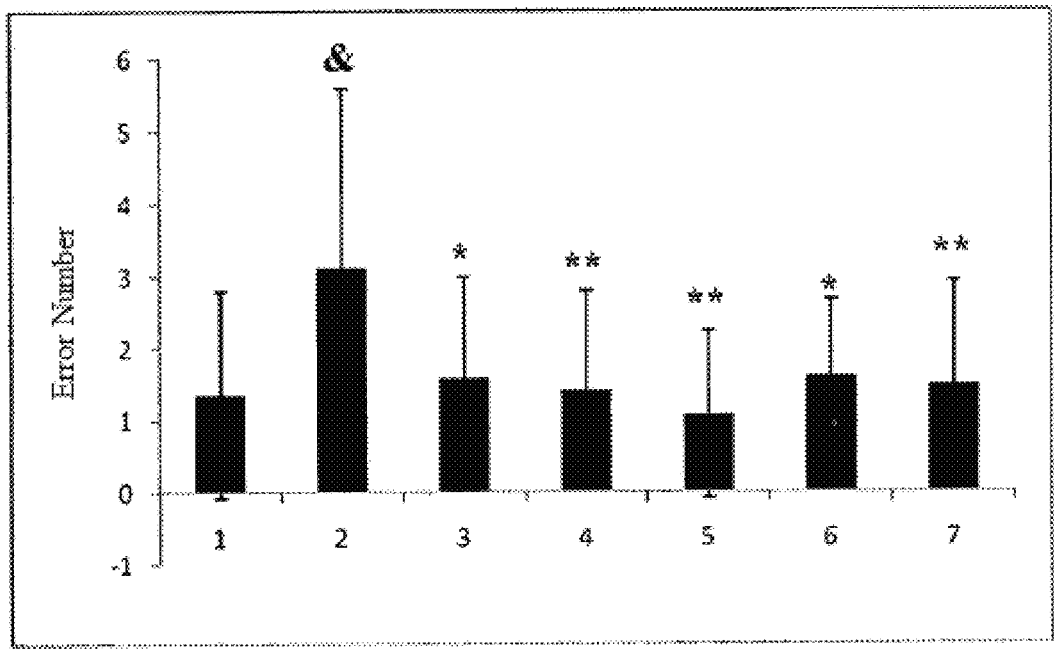
FIG. 14 shows influence of the beautyberry total glycosides extract on the number of step down errors of scopolamine induced mice, wherein 1: a blank control group; 2: a model group; 3: a *Callicarpa kochiana* total glycosides group (300 mg/kg); 4: a low dose group (100 mg/kg) of the beautyberry total glycosides extract of Example 6 of the present invention; 5: a high dose group (300 mg/kg) of the beautyberry total glycosides extract of Example 6 of the present invention; 6: a low dose group (100 mg/kg) of the beautyberry total glycosides extract of Example 7 of the present invention; 7: a high dose group (300 mg/kg) of the beautyberry total glycosides extract of Example 7 of the present invention; "&&" denotes P<0.01 as compared with the blank control group, "*" denotes p<0.05 as compared with the model group, "**" denotes p<0.01 as compared with the model group, and "#" denotes P<0.05 as compared with the *Callicarpa kochiana* total glycosides group.

As shown in FIGS. 13 and 14, mice in the model group have significantly shortened latency (p<0.05) and significantly increased error number (p<0.05), as compared with the blank control group, suggesting that disorders had occurred in learning and memory acquisition of the mice after scopalamine treatment. For the *Callicarpa kochiana* total glycosides group (300 mg/kg), the latency increased (P<0.05) and the error number decreased (p<0.05) as compared with the model group. In the high dose group (300 mg/kg) and the low dose group (100 mg/kg) of the beautyberry total glycosides extract of Example 6 in the present invention, the latency significantly increased (p<0.01), and the error number significantly decreased (P<0.01) compared to the model group. In the high dose group (300 mg/kg) of the beautyberry total glycosides extract of Example 7 in the present invention, the latency tested of the mice can be significantly increased (P<0.01), and the error number can be significantly reduced (P<0.01), as compared with the model group. In the low dose group (100 mg/kg) of the beautyberry total glycosides extract of Example 7 in the present invention, the latency tested of the mice can be increased (p<0.05), and the error number can be reduced (P<0.05). The high dose group (300 mg/kg) of the high-concentration beautyberry total glycosides extract of Example 6 in the present invention has a better effect as compared with the *Callicarpa kochiana* total glycosides group (300 mg/kg) (P<0.05).

Example 13

Therapeutic effect of the beautyberry total glycosides extract of the present invention against dinitrochlorobenzol (DNCB) induced chronic dermatitis—eczema in mice 1. Material and Method
   1.1 Animal Animals were male Kunming mice of 7-week age, with body weight of 18 to 22 g, supplied by Shanghai Slaccas Experimental Animal LimitedLiabilityCompany. Certification number: 2007000539123.

1.2 Drug and Reagent

The beautyberry total glycosides extracts prepared in Examples 6 and 8 were tested, wherein the beautyberry total glycosides extract obtained in Example 6 contained 45.06 wt % verbascoside and 40.25 wt % Arenarioside, and the beautyberry total glycosides extract obtained in Example 8 contained 19.23 wt % verbascoside and 15.95 wt % Arenarioside. The beautyberry total glycosides extracts were added respectively into hot-melt vaseline to formulate samples of 10%. 2,4-dinitrochlorobenzene (DNCB): analytically pure, from Chengdu Gracia Chemical Technology Co., LTD, 201205147) was formulated, using acetone, into 7 w/v % and 0.5 w/v % solutions. 999 Piyanping ointment (Sanjiu Medical & Pharmaceutical Company, batch number 1203044H). Interleukin-2 (IL-2) and tumor necrosis factor-α (TNF-α) radioimmunoassay kits (Rapidbio (RB) Company, U.S.A., batch number: 201210). Other reagents were all domestic chemically pure reagents.

1.3 Instrument

A Codos electric clipper for pet (model: CP-7800); a micro-pipettor (eppendorf, Germany); a Bio-Tec microplate reader (ELX-800, U.S.A.); a carbon dioxide incubator (SANYO, MCO-18AIC (UV)); a Hitachi centrifuge (HI-CATHI, CT15E).

2. Preparation of a Model of Dinitrochlorobenzol Induced Dermatitis—Eczema in Mice on Back Thereof Abdomens of the mice were shaved on skin with area of about 2 cm×2 cm 1 day before experiment. On day 1 of the experiment, 25 μl of a 7 w/v % DNCB acetone solution was smeared on the shaved area of abdomen of the mouse for sensitization. On day 5 of the experiment, back of the mouse was shaved, and areas of about 1 cm×1 cm on both left and right parts of the back were selected for later use. Since day 6, 20 μl of a 0.5 w/v % DNCB solution was smeared on the shaved areas on both left and right parts of the back of the mouse for challenging, which was performed once every other 3 days, totally 4 times. The evident occurrence of phenomena such as skin roughening, incrassation, ichenification, flushing, erythema, keratinization, and damage in the skin on the back of the mouse indicated successful modeling.

3. Animal Grouping and Dosage 8 of 40 mice were assigned to a blank control group (Group A), the remaining 32 mice were used in the preparation of the mouse dermatitis—eczema models. After successful modeling, the 32 mice were randomly assigned into 8 groups: group a model group (Group B, receiving 250 mg of vaseline blank matrix), a positive control group of 999 Piyanping ointment (Group C, receiving 500 mg of the ointment/kg, equivalent to 0.375 mg/kg dexamethasone acetate), beautyberry total glycosides extract example 6 group (Group D, receiving the beautyberry total glycosides extract of Example 6 in the present invention 250 mg/kg), and beautyberry total glycosides extract example 68 group (Group E, receiving beautyberry total glycosides extract of Example 8 in the present invention 250 mg/kg). Each group has with 8 mice. Since day 2 of successful modeling, drugs were uniformly smeared on left and right parts of the back of the mice twice/day for 14 continuous days.

4. Measurement Indexes and Method 4.1 Effects on Animal Behaviour

The presence or absence of effects of medication on general conditions such as body mass, hair color, diet, and activity of the mice waere observed, durin the the experiment.

4.2 Morphological Change in Skin 24 h after successful modeling and during the treatment process respectively, cutaneous reactions at the challenged site and morphological changes in skin damage of the mouse were observed, and observation indexes included roughening, incrassation, ichenification, flushing, erythema, keratinization, damage and the like.

4.3 Histopathological Examination

After completion of the treatments, skins at damaged sites of mice in each group were clipped out, and full-thickness skin was trephined. Circular specimen having a diameter of 0.3 cm were collected at the damaged sites at the left and right back of the mouse and prepared for paraffin slides which were then stained with HE. The slides were microscopically examined for histopathological changes in the skin. The quantity of inflammatory cell infiltration in the dermis layer per unit of the field under microscope was counted using a net-type ocular. Each group had a total of 20 slides and each slide was examined for 5 high power fields (×200).

4.4 Effects on Cell Factors in Serum

Blood was collected by extraction of eyeballs of the mice, naturally coagulated at room temperature for 10 to 20 min, and was centrifugated at 3000 rpm for 20 min. Then the supernatant was collected carefully. Detection of IL-2 and TNF-α was carried out following manufacturer's instructions of the IL-2 and TNF-α kits.

5. Results 5.1 Effects on the General Behavior

During the experiment no statistical difference in body mass of mice was observed among groups. No changes in hair color or diet were observed either. In the experimental groups, the mice often scratched with ear agitation after sensitization and challenging. No animal died during the observation period.

5.2 Effects on Skin Morphology

Figure 15:
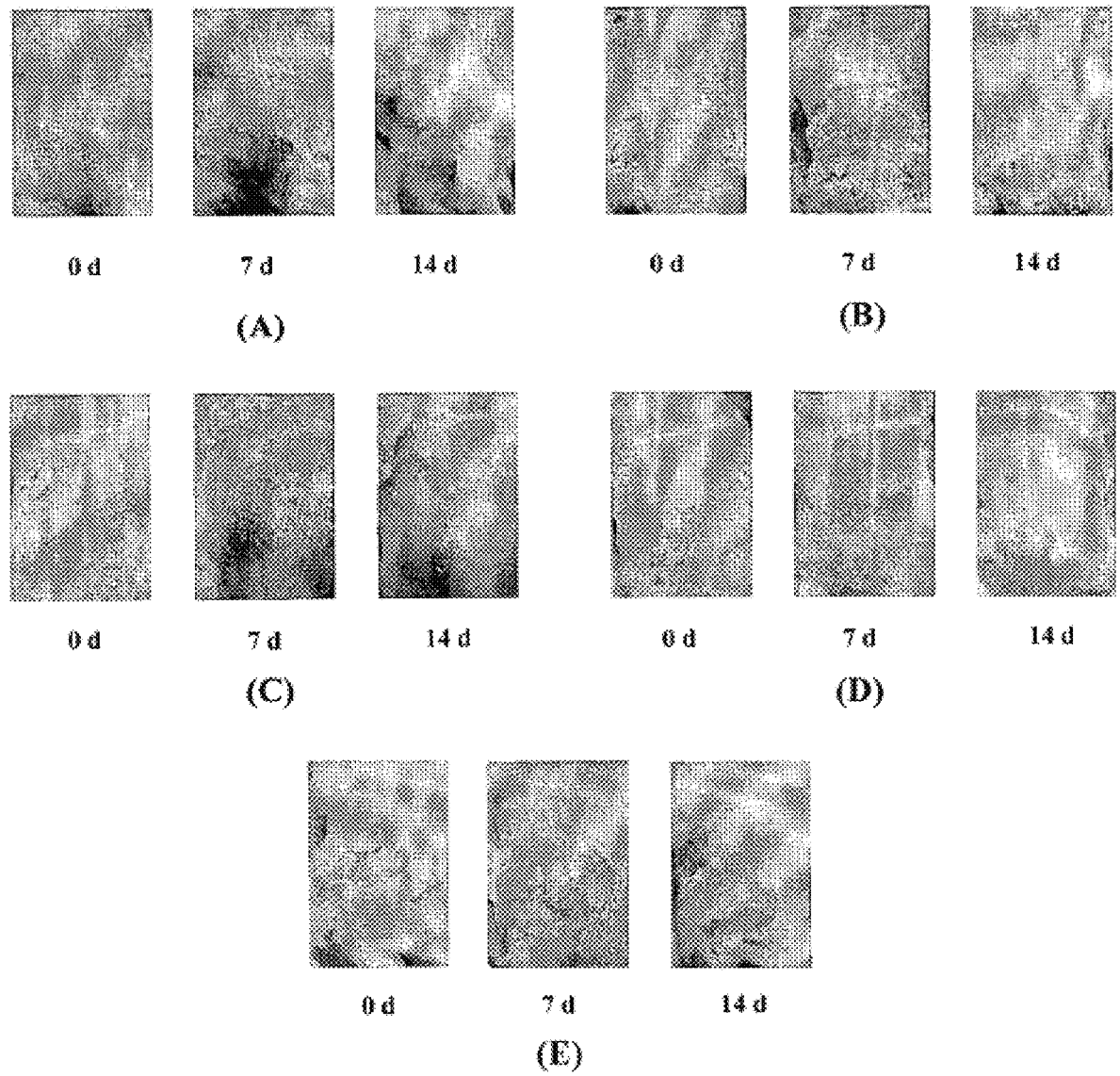
FIG. 15 shows therapeutic effects of the beautyberry total glycosides extract of the present invention and the positive control drug on the skin dermatitis—eczema model on the back of DNCB induced mice at different dosage time, wherein A: a blank control group; B: a model group; C: a 999 Piyanping ointment positive control group (500 mg of the ointment/kg; equivalent to 0.375 mg/kg dexamethasone acetate); D: a group (250 mg/kg) of the beautyberry total glycosides extract of Example 6 of the present invention; and E: a group (250 mg/kg) of the beautyberry total glycosides extract of Example 8 of the present invention.

After challenged with DNCB, eczematoid reaction occurred on the back of the mice, which manifested as phenomenons such as diffuse erythema edema. There were roughness, scratches, flushed, blood scabs, keratinization and obscure boundary on the DNCB applied area on the skin. 7 days after drug treatment, animals in groups receiving drugs had abated erythema and edema. 14 days after drug treatment, erythema was further abated, and the skin of some drug treated mice was returned to normal (FIG. 15).

Figure 16:
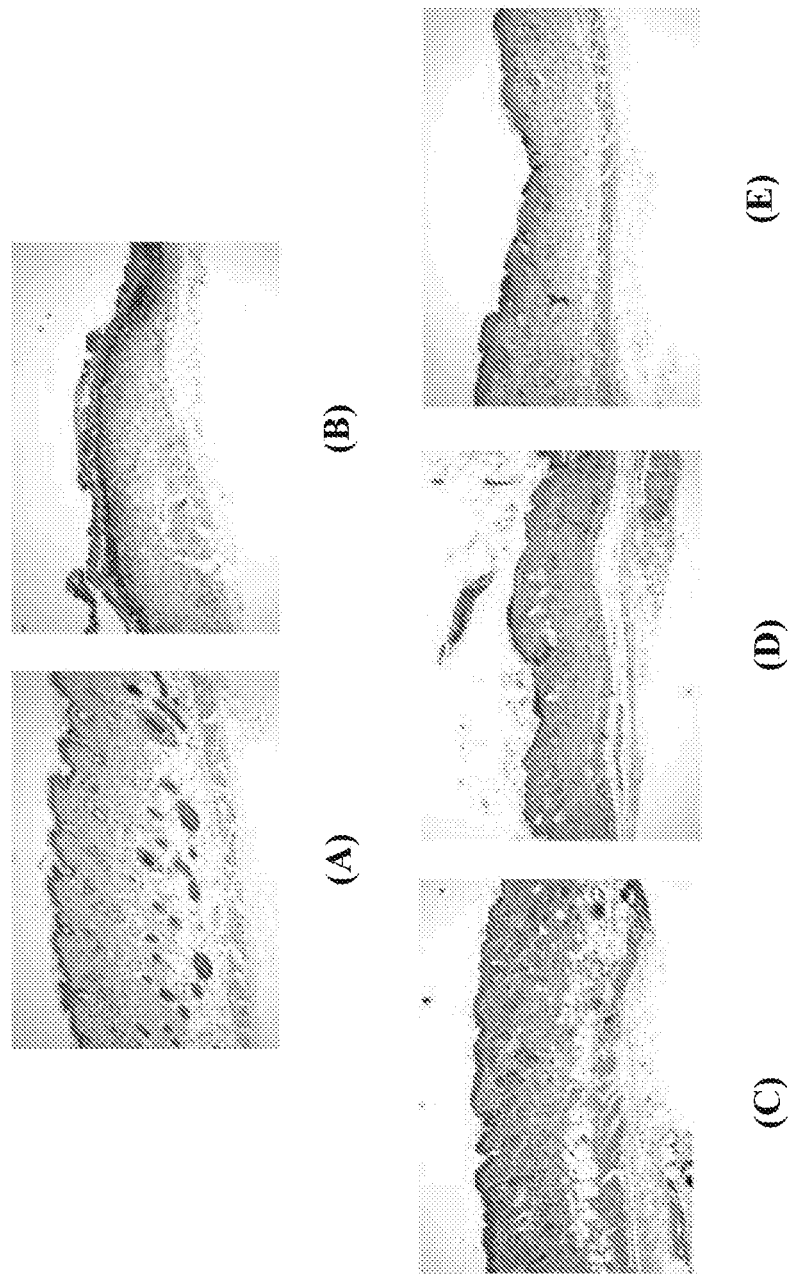
FIG. 16 shows photographs of skin pathological tissues of the mice in each group, wherein A: a blank control group; B: a model group; C: a 999 Piyanping ointment positive control group (500 mg of the ointment/kg; equivalent to 0.375 mg/kg dexamethasone acetate); D: a group (250 mg/kg) of the beautyberry total glycosides extract of Example 6 of the present invention; and E: a group (250 mg/kg) of the beautyberry total glycosides extract of Example 8 of the present invention.

5.3 Histopathological Examination 5.3.1 Effects on Skin Lesions in Dermatitis—Eczema Model Mice In the model group, epidermis of the mice showed moderate keratinization, focal parakeratosis, ocal epidermal necrosis, significantly incrassated epidermis, increased prickle cell layers, swelling of part of prickle cells, spongiosis, and increased inflammatory cells from epidermis to derma; In each of the dosage groups and the positive control groups, pathological manifestations such as epidermal keratinization, incrassation of prickle cell layers, and infiltration of inflammatory cells were all ameliorated to varying degrees, seen in FIG. 16.

5.3.2 Effects on the Inflammatory Cell Count in Derma of Mice

Figure 17:
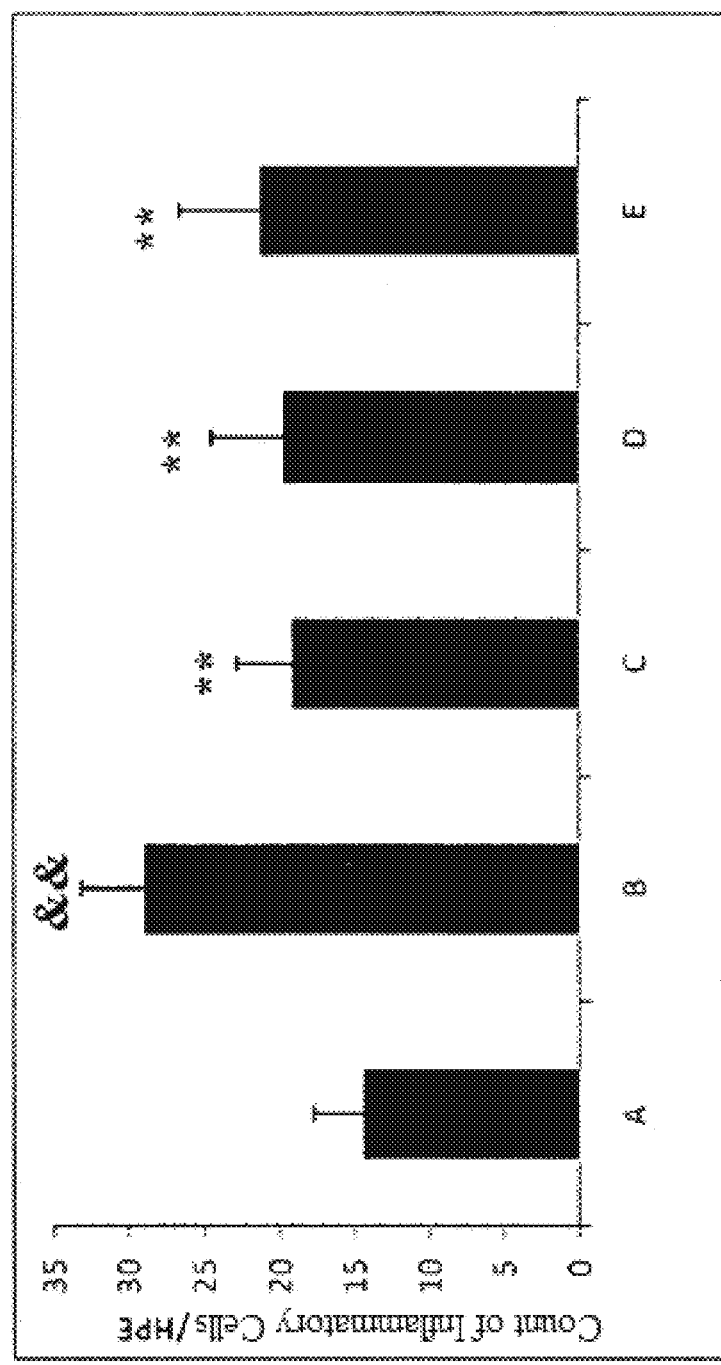
FIG. 17 shows influence of the beautyberry total glycosides extract of the present invention on inflammatory cells within derma of the dermatitis—eczema model, wherein A: a blank control group; B: a model group; C: a 999 Piyanping ointment positive control group (500 mg of the ointment/kg; equivalent to 0.375 mg/kg dexamethasone acetate); D: a group (250 mg/kg) of the beautyberry total glycosides extract of Example 6 of the present invention; and E: a group (250 mg/kg) of the beautyberry total glycosides extract of Example 8 of the present invention. "&&" denotes P<0.01 as compared with the blank control group, and "**" denotes p <0.01 as compared with the model group.

As shown in FIG. 17 the inflammatory cell count in derma of mice in the model group was significantly increased. In contrast, the inflammatory cell count in derma of mice receiving extracts was significantly decreased as compared with the model group and had significant difference (P<0.01). The beautyberry total glycosides extract group had no significant difference as compared with the positive control group.

5.4 Effects on Cell Factors in Serum

Figure 18:
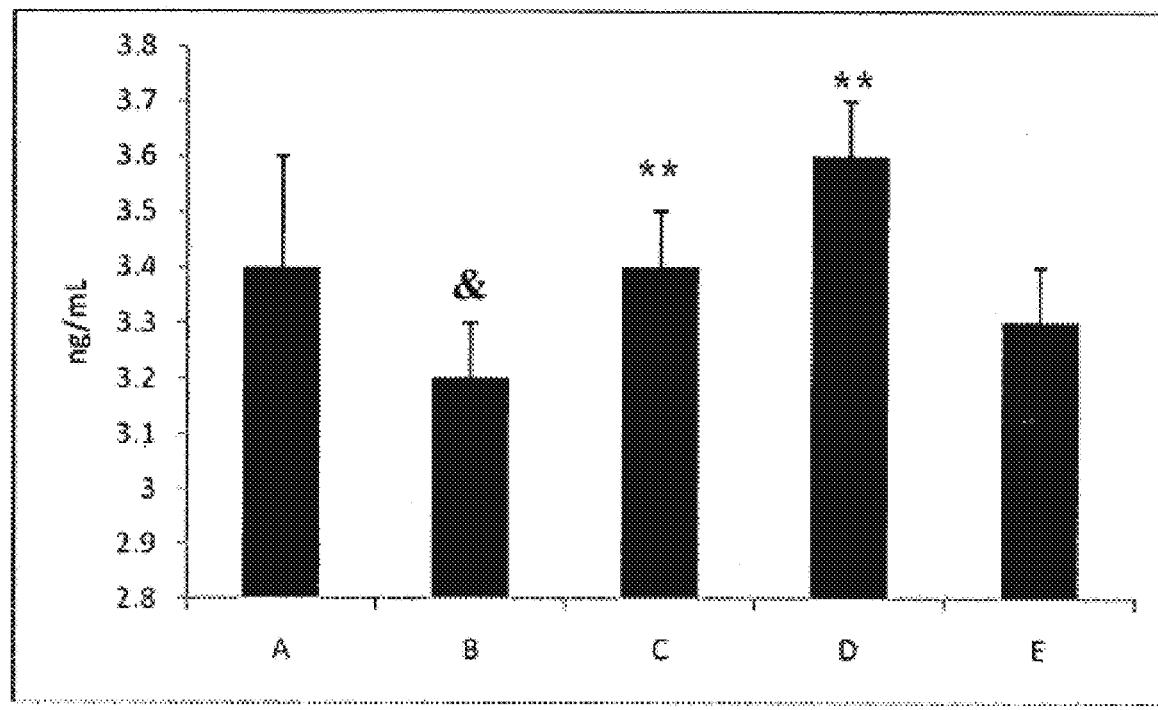
FIG. 18 shows influence of the beautyberry total glycosides extract of the present invention on IL-2 (a) and TNF-α (b) in serum of the dermatitis—eczema model mice, wherein A: a blank control group; B: a model group; C: a 999 Piyanping ointment positive control group (500 mg of the ointment/kg; equivalent to 0.375 mg/kg dexamethasone acetate); D: a group (250 mg/kg) of the beautyberry total glycosides extract of Example 6 of the present invention; and E: a group (250 mg/kg) of the beautyberry total glycosides extract of Example 8 of the present invention. "&" denotes P<0.05 as compared with the blank control group, "&&" denotes P<0.01 as compared with the blank control group, "*" denotes p<0.05 as compared with the model group, and "**" denotes p<0.01 as compared with the model group.
Figure 18:
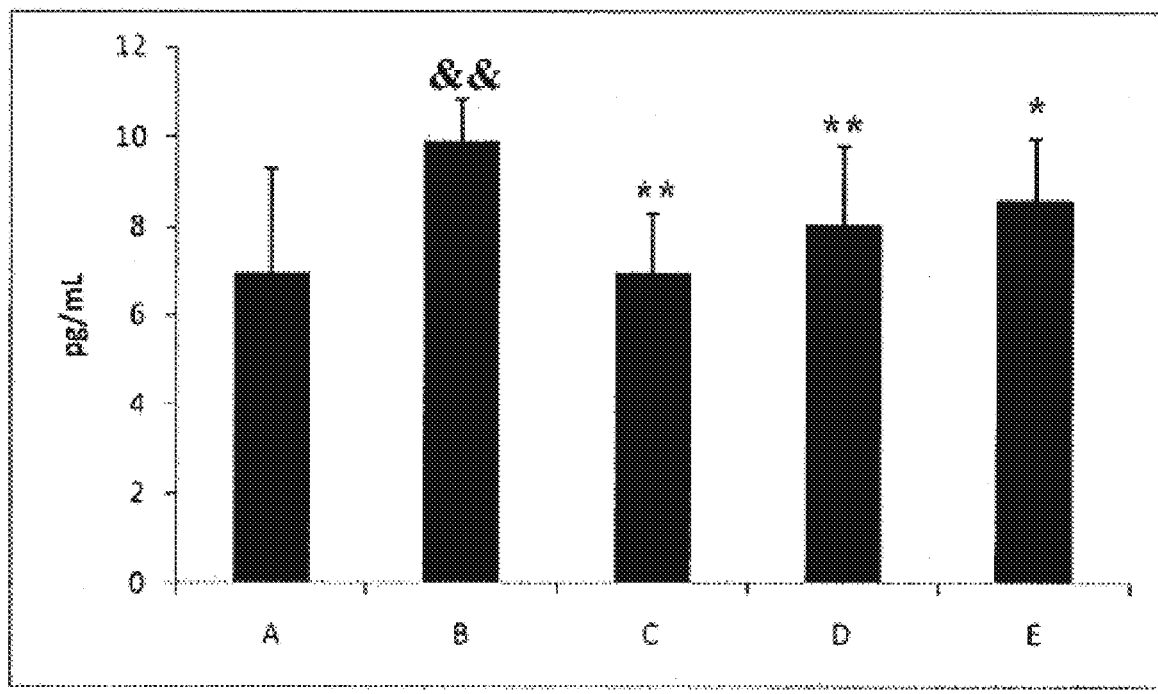

As shown in FIG. 18, the IL-2 concentration level in serum of mice in the model group was significantly decreased as compared with the blank control group (P <0.05). The IL-2 levels in serum of mice in each drug group all increased as compared with the model group, wherein the Piyanping ointment group and the group of the beautyberry total glycosides extract prepared in Example 6 of the present invention have the most significant difference as compared with the model group (P<0.01). The group of the beautyberry total glycosides extract prepared in Example 8 of the present invention has no significant difference as compared with the model group.

The TNF-α level in serum of mice in the model group significantly increased as compared with the blank control group (P<0.01). The IL-2 levels in serum of mice receiving the extracts of the present invention and the positive control drug all decreased as compared with the model group. The Piyanping ointment group and the group of the beautyberry total glycosides extract prepared in Example 6 of the present invention had significant lower level of TNF-α as compared with the model group (P <0.01). The group of the beautyberry total glycosides extract prepared in Example 8 of the present invention had lower level of TNF-α difference as compared with the model group (P<0.05).

The description of the above embodiments and examples of the present invention is only for the purpose of illustration and explanation, and does not limit the present invention in any way. Evidently, various modifications and changes may be made by those of skill in the art according to the teachings given in the context of the present invention. All of these modifications and changes fall with the spirit and scope of the present invention defined by the claims.

What is claimed is:

1. A method for preparing a beautyberry total glycosides extract, comprising:
    (a) pulverizing leaves of Callicarpa cathayana H.T. Chang;
    (b) extracting said leaves with a solvent 1 to 3 times, wherein said solvent comprises water;
    (c) combining extract liquors from each extraction to form combined extract liquors, then concentrating said combined extract liquors under reduced pressure to remove said solvent and form concentrated combined extract liquors;
    (d) adding water in an amount of 0.5 to 2 times the volume of said concentrated combined extract liquors to said concentrated combined extract liquors, then letting said combined extract liquor and water mixture stand overnight;
    (e) centrifuging or filtering said combined extract liquor and water mixture to obtain a supernatant; and
    (f) passing said supernatant through a chromatographic column packed with a resin filler, washing with water and/or a dilute alcohol aqueous solution of up to 15% vol alcohol, then eluting with an alcohol aqueous solution with a higher concentration of alcohol, collecting eluent, concentrating under reduced pressure, and drying, so as to obtain said beautyberry total glycosides extract.

2. The method of claim 1, wherein in step (b) said extraction method comprises a flash extraction method, a reflux extraction method, a microwave extraction method, an ultrasonic extraction method, or a percolation extraction method.

3. The method of claim 2, wherein in step (f), said resin filler comprises macroporous adsorbent resin, a polyamide resin or an ion exchange resin.

4. The method of claim 3, wherein in step (f), said alcohol aqueous solution with a higher concentration of alcohol is a 30 to 90 vol % alcohol aqueous solution.

5. The method of claim 1, wherein in step (f), the following operation is performed one or more times after the concentration of the eluent under reduced pressure: the concentrated solution is dissolved with water, allowed to pass through the chromatographic column, washed with water and/or a dilute alcohol aqueous solution of up to 15% vol alcohol to remove impurities, and then eluted with a high concentration an alcohol aqueous solution with a higher concentration of alcohol, and the eluent is collected.

6. The method of claim 5, wherein said collected eluent is collected and concentrated under reduced pressure.

* * * * *